United States Patent
Lee et al.

(10) Patent No.: US 9,416,107 B2
(45) Date of Patent: Aug. 16, 2016

(54) HETEROCYCLIC COMPOUND AND ORGANIC LIGHT-EMITTING DEVICE INCLUDING THE SAME

(75) Inventors: Sun-Young Lee, Yongin (KR); Yoon-Hyun Kwak, Yongin (KR); Bum-Woo Park, Yongin (KR); Hee-Joo Ko, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 915 days.

(21) Appl. No.: 13/272,701

(22) Filed: Oct. 13, 2011

(65) Prior Publication Data

US 2013/0001522 A1 Jan. 3, 2013

(30) Foreign Application Priority Data

Jun. 29, 2011 (KR) ........................ 10-2011-0064075

(51) Int. Cl.
*H01L 51/54* (2006.01)
*C07D 221/18* (2006.01)
(Continued)

(52) U.S. Cl.
CPC ............ *C07D 221/18* (2013.01); *C07D 401/10* (2013.01); *C07D 401/14* (2013.01); *C07D 487/04* (2013.01); *C09K 11/06* (2013.01); *H01L 51/0072* (2013.01); *H05B 33/14* (2013.01); *C09K 2211/1007* (2013.01); *C09K 2211/1011* (2013.01); *C09K 2211/1029* (2013.01);
(Continued)

(58) Field of Classification Search
CPC .. C07D 401/14; C07D 401/10; C07D 487/04; C07D 221/18; C09K 11/06; C09K 2211/1092; C09K 2211/1007; C09K 2211/1011; C09K 2211/1029; C09K 2211/1044; C09K 2211/1088; H01L 51/0072; H01L 51/5012; H01L 51/5016; H05B 33/14
See application file for complete search history.

(56) References Cited

U.S. PATENT DOCUMENTS 5,635,308 A 6/1997 Inoue et al.
5,645,948 A 7/1997 Shi et al.
(Continued)

FOREIGN PATENT DOCUMENTS

JP 8-12600 1/1996
JP 2000-3782 1/2000
(Continued)

OTHER PUBLICATIONS

Journal of Physical Chemistry A (2003), 107 (10), pp. 1486-1498.*
(Continued)

*Primary Examiner* — Dawn Garrett
(74) *Attorney, Agent, or Firm* — Robert E. Bushnell, Esq.

(57) ABSTRACT

A heterocyclic compound represented by Formula 1 below and an organic light-emitting device including the same:

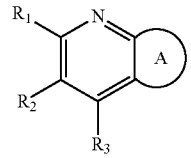

Formula 1 wherein Formula 1 is defined as in the detailed description.

14 Claims, 1 Drawing Sheet

| SECOND ELECTRODE |
|---|
| EIL |
| ETL |
| EML |
| HTL |
| HIL |
| FIRST ELECTRODE |

(51) Int. Cl.
*C07D 401/10* (2006.01)
*C07D 401/14* (2006.01)
*C07D 487/04* (2006.01)
*C09K 11/06* (2006.01)
*H01L 51/00* (2006.01)
*H05B 33/14* (2006.01)
*H01L 51/50* (2006.01)

(52) U.S. Cl.
CPC . *C09K2211/1044* (2013.01); *C09K 2211/1088* (2013.01); *C09K 2211/1092* (2013.01); *H01L 51/5012* (2013.01); *H01L 51/5016* (2013.01)

(56) References Cited

U.S. PATENT DOCUMENTS

| | | | |
|---|---|---|---|
| 5,972,247 A | 10/1999 | Shi et al. | |
| 6,465,115 B2 | 10/2002 | Shi et al. | |
| 6,596,415 B2 | 7/2003 | Shi et al. | |
| 7,858,724 B2 | 12/2010 | Kanitz et al. | |
| 2004/0076853 A1* | 4/2004 | Jarikov | 428/690 |
| 2004/0124766 A1* | 7/2004 | Nakagawa et al. | 313/504 |
| 2008/0224129 A1* | 9/2008 | Choi et al. | 257/40 |
| 2012/0153269 A1* | 6/2012 | Horiuchi | H01L 51/0072 257/40 |
| 2013/0001527 A1* | 1/2013 | Han | C07D 401/14 257/40 |
| 2013/0119353 A1* | 5/2013 | Zeng | H01L 51/0094 257/40 |

FOREIGN PATENT DOCUMENTS

| | | |
|---|---|---|
| KR | 10-2006-0127101 A | 12/2006 |
| KR | 10-0686109 B1 | 2/2007 |
| KR | 10-0699096 B1 | 3/2007 |
| KR | 10-2010-0003624 A | 1/2010 |
| KR | 10-2010-0108924 A | 10/2010 |

OTHER PUBLICATIONS

Derwent abstract for CN 103540313 A, publication date Jan. 2014.*
Adachi et al., Confinement of charge carriers and molecular excitons within 5-nm-thick emitter layer in organic electroluminescent devices with a double heterostructure, Appl. Phys. Lett (1990) 57, pp. 531-533.
Sakamoto et al., Synthesis, Characterization, and Electron-Transport Property of Perlluorinated Phenylene Dendrimers, J. Am. Chem. Soc. (2000) 122, pp. 1832-1833.
Tang et al., Organic electroluminescent diodes, Appl. Phys. Lett. (1987) 51, pp. 913-915.
Yamaguchi et al., Diphenylamino-Substituted 2,5-Diarylsiloles for Single-Layer Organic Electroluminescent Devices, Chem. Lett. (2001) pp. 98-99.

* cited by examiner

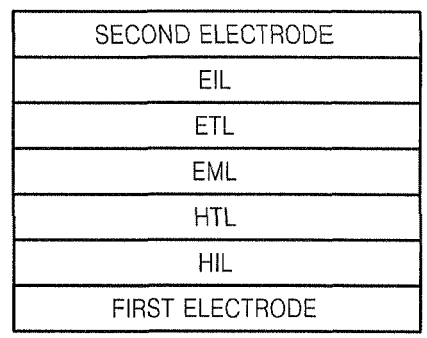

HETEROCYCLIC COMPOUND AND ORGANIC LIGHT-EMITTING DEVICE INCLUDING THE SAME

CLAIM OF PRIORITY

This application claims the benefit of Korean Patent Application No. 10-2011-0064075, filed on Jun. 29, 2011, in the Korean Intellectual Property Office, the disclosure of which is incorporated herein in its entirety by reference.

BACKGROUND OF THE INVENTION

1. Field of the Invention

The present invention relates to a heterocyclic compound and an organic light-emitting device including the same.

2. Description of the Related Art

Light-emitting devices are self-emission type display devices and have a wide viewing angle, a high contrast ratio, and a short response time. Due to these characteristics, light-emitting devices are drawing more attention. Such light-emitting devices can be roughly classified into inorganic light-emitting devices that include emission layers containing inorganic compounds, and organic light-emitting devices that include emission layers containing organic compounds. Specifically, organic light-emitting devices have higher luminance, lower driving voltages, and shorter response times than inorganic light-emitting devices, and can render multi-colored displays. Thus, much research into such organic light-emitting devices has been conducted. Typically, an organic light-emitting device has a stack structure including an anode, a cathode and an organic emission layer interposed therebetween. However, a hole injection layer and/or a hole transport layer may be further stacked between the anode and the organic emission layer, and/or an electron transport layer may be further stacked between the organic emission layer and the cathode. In other words, an organic light-emitting device may have a stack structure of anode/hole transport layer/organic emission layer/cathode or a stack structure of anode/hole transport layer/organic emission layer/electron transport layer/cathode.

Anthracene derivatives are widely known as materials for organic light-emission layer materials. However, organic light-emitting devices including these materials are not yet satisfactory to meet requirements in terms of lifespan, efficiency, and power consumption, thereby improvement in this regard still being necessary.

SUMMARY OF THE INVENTION

The present invention provides a novel heterocyclic compound having good electrical characteristics, charge transporting capabilities, and light-emission capabilities.

The present invention provides an organic light-emitting device including the heterocyclic compound.

The present invention provides a flat panel display device including the organic light-emitting device.

According to an aspect of the present invention, there is provided a heterocyclic compound represented by Formula 1 below:

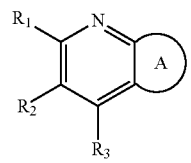

Formula 1 wherein, $R_1$ to $R_3$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, an amino group substituted with a $C_5$-$C_{60}$ aryl group or a $C_3$-$C_{60}$ heteroaryl group, a substituted or unsubstituted $C_3$-$C_{60}$ heteroaryl group, a substituted or unsubstituted $C_6$-$C_{60}$ fused polycyclic group, a halogen atom, a cyano group, a nitro group, a hydroxyl group, or a carboxyl group, and A is a substituted or unsubstituted phenanthrene group.

The heterocyclic compound may be represented by Formula 2 or 3 below:

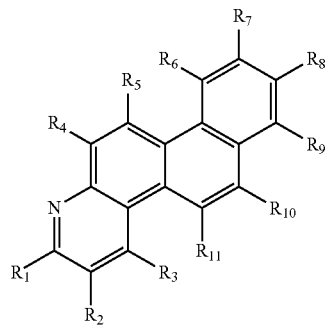

Formula 2

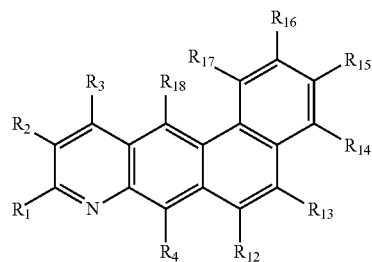

Formula 3 wherein $R_1$ to $R_{18}$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, an amino group substituted with a $C_5$-$C_{60}$ aryl group or a $C_3$-$C_{60}$ heteroaryl group, a substituted or unsubstituted $C_3$-$C_{60}$ heteroaryl group, a substituted or unsubstituted $C_6$-$C_{60}$ fused polycyclic group, a halogen atom, a cyano group, a nitro group, a hydroxyl group, or a carboxyl group.

In Formulae 2 and 3, $R_1$ to $R_{18}$ may be each independently a hydrogen atom, a deuterium atom, a cyano group, a halogen atom, a substituted or unsubstituted $C_1$-$C_{20}$ alkyl group, a substituted or unsubstituted $C_5$-$C_{40}$ aryl group, a substituted or unsubstituted $C_3$-$C_{40}$ heteroaryl group, an amino group substituted with a $C_5$-$C_{40}$ aryl group or a $C_3$-$C_{20}$ heteroaryl group, or a substituted or unsubstituted $C_6$-$C_{40}$ fused polycyclic group.

In Formulae 2 and 3, $R_1$ to $R_{18}$ may be each independently a hydrogen atom, a deuterium atom, a halogen atom, a cyano group, a substituted or unsubstituted $C_1$-$C_{20}$ alkyl group, or groups represented by Formulae 2a to 2g below:

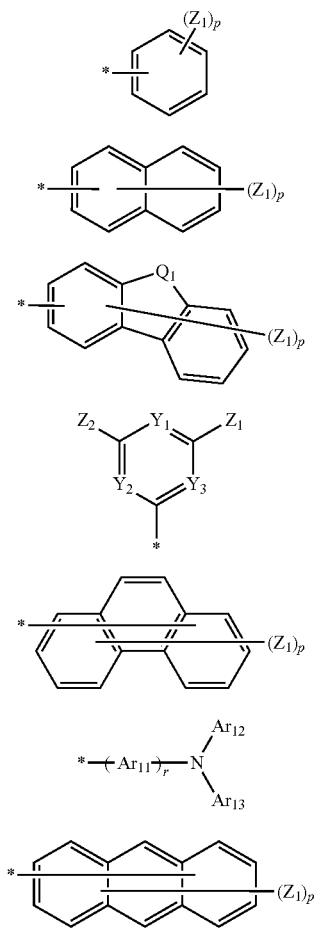

wherein $Q_1$ is a linking group selected from among —C($R_{19}$)($R_{20}$)—, —S— and —O—; $Y_1$, $Y_2$ and $Y_3$ are each independently a linking group selected from among —N= and —C($R_{22}$)=; $Z_1$, $Z_2$, $Ar_{12}$, $Ar_{13}$, $R_{19}$, $R_{20}$, $R_{21}$ and $R_{22}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; $Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group; p is an integer from 1 to 7; r is an integer from 0 to 5; and * indicates a binding site.

In Formulae 2 and 3, $R_1$ to $R_{18}$ may be each independently a hydrogen atom, a deuterium atom, a halogen atom, a cyano group, a methyl group, an ethyl group, a propyl group, a butyl group, a pentyl group, or groups represented by Formulae 3a to 3c below:

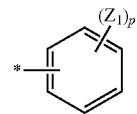

3a

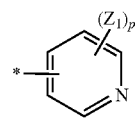

3b

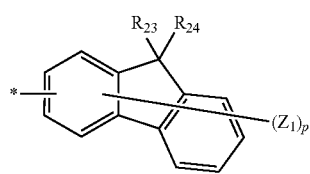

3c wherein $Z_1$, $R_{23}$ and $R_{24}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; p is an integer from 1 to 7; and * indicates a binding site.

In Formulae 2 and 3, $R_1$, $R_2$, $R_3$, $R_5$, $R_6$, $R_7$, $R_8$, $R_9$, $R_{11}$, $R_{12}$, $R_{14}$, $R_{15}$, $R_{16}$, $R_{17}$ and $R_{18}$ may be each independently a hydrogen atom or a deuterium atom.

In Formulae 2 and 3, $R_1$, $R_2$, $R_3$, $R_5$, $R_6$, $R_7$, $R_8$, $R_9$, $R_{11}$, $R_{12}$, $R_{14}$, $R_{15}$, $R_{16}$, $R_{17}$ and $R_{18}$ may be each independently a hydrogen atom or a deuterium atom, and $R_4$, $R_{10}$ and $R_{13}$ are each independently a hydrogen atom, a deuterium atom, a halogen atom, a cyano group, a substituted or unsubstituted $C_1$-$C_{20}$ alkyl group, or groups represented by Formulae 2a to 2g below:

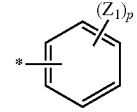

2a

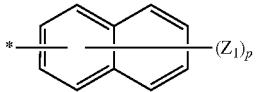

2b

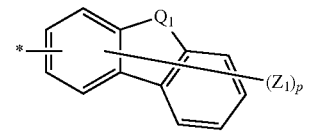

2c

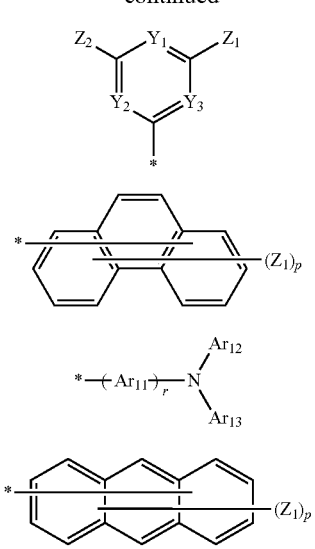

2d

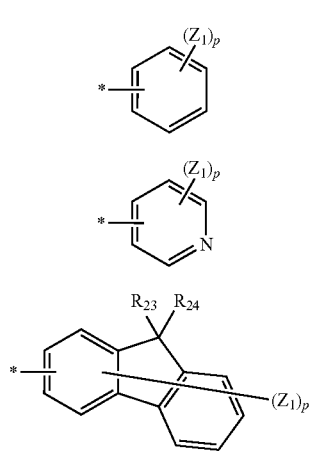

2e

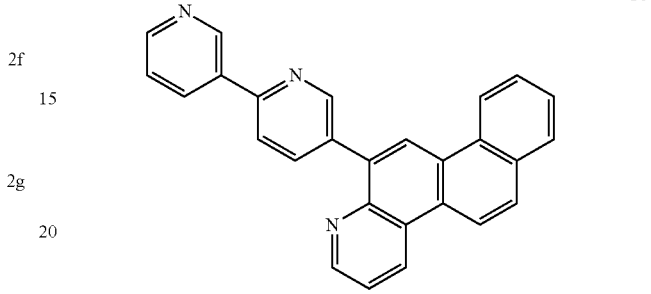

wherein $Q_1$ is a linking group selected from among —C($R_{19}$)($R_{20}$)—, —S— and —O—; $Y_1$, $Y_2$ and $Y_3$ are each independently a linking group selected from among —N= and —C($R_{22}$)=; $Z_1$, $Z_2$, $Ar_{12}$, $Ar_{13}$, $R_{19}$, $R_{20}$, $R_{21}$ and $R_{22}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; $Ar_{11}$ is a substituted or unsubstituted alkylene group, a substituted or unsubstituted $C_5$-$C_{20}$ arylene group, or a substituted or unsubstituted $C_3$-$C_{20}$ heteroarylene group; p is an integer from 1 to 7; r is an integer from 0 to 5; and * indicates a binding site.

In Formulae 2 and 3, $R_1$, $R_2$, $R_3$, $R_5$, $R_6$, $R_7$, $R_8$, $R_9$, $R_{11}$, $R_{12}$, $R_{14}$, $R_{15}$, $R_{16}$, $R_{17}$ and $R_{18}$ may be each independently a hydrogen atom and a deuterium atom, and $R_4$, $R_{10}$ and $R_{13}$ are each independently a hydrogen atom, a deuterium atom, a halogen atom, a cyano group, a methyl group, an ethyl group, a propyl group, a butyl group, a pentyl group, or groups represented by Formulae 3a to 3c below:

3a

3b

3c wherein $Z_1$, $R_{23}$ and $R_{24}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; p is an integer from 1 to 7; and * indicates a binding site.

The heterocyclic compound may be any one of compounds below:

18

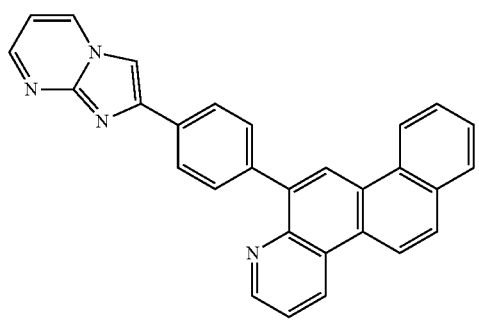

19

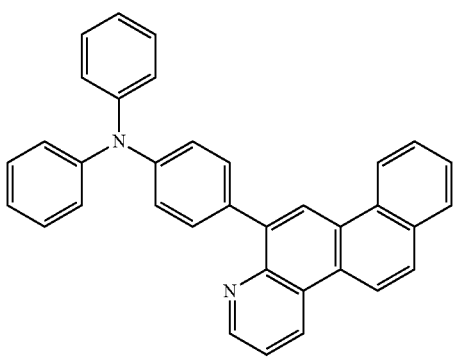

22

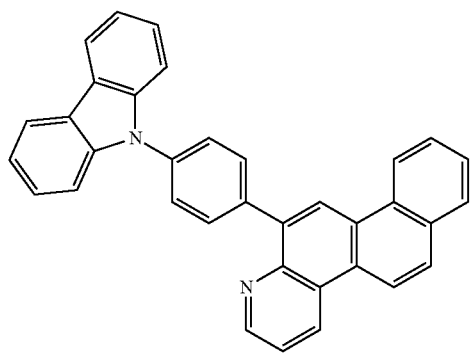

32

37

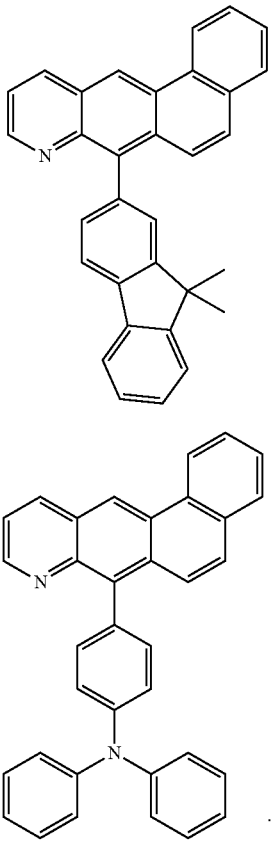

39

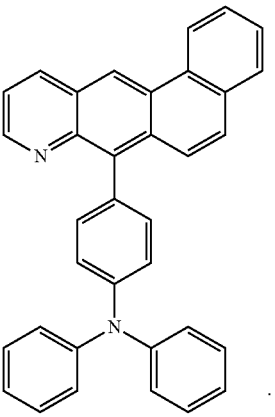

According to another aspect of the present invention, there is provided an organic light-emitting device including a first electrode; a second electrode; and an organic layer interposed between the first electrode and the second electrode, wherein the organic layer includes the heterocyclic compound.

The first layer may include a hole injection layer (HIL); a hole transport layer (HTL); a layer having both a hole injection function and a hole transport function; an electron injection layer (EIL); an electron transport layer (ETL); or a layer having both an electron injection function and an electron transport function.

The first layer may include a hole injection layer (HIL); a hole transport layer (HTL); a layer having both a hole injection function and a hole transport function; an emission layer (EML); an electron injection layer (EIL); an electron transport layer (ETL); and a layer having both an electron injection function and an electron transport function, wherein the first layer further includes a charge-generating material.

The first layer may be an emission layer (EML), and the heterocyclic compound may be used as a host or a dopant.

The first layer may be an emission layer (EML), and the EML may further include an anthracene compound, an arylamine compound or a styryl compound.

The first layer may be an emission layer (EML), and any one of a red layer, a green layer, a blue layer, and a white layer of the EML may include a phosphorescence compound.

The first layer may be a blue emission layer.

The first layer may be a blue emission layer, and the heterocyclic compound may be used as a blue dopant.

The organic layer may further include a hole injection layer (HIL), a hole transport layer (HTL), a layer having both a hole injection function and a hole transport function, an emission layer (EML), a hole block layer (HBL), an electron transport layer (ETL), an electron injection layer (EIL), or a combination of at least two thereof.

The first layer may be formed by using a wet method using the heterocyclic compound.

According to another aspect of the present invention, there is provided a flat panel display device including the organic light-emitting device, wherein the first electrode of the organic light-emitting device is electrically connected to a source electrode or a drain electrode of a thin film transistor.

BRIEF DESCRIPTION OF THE DRAWINGS

The above and other features and advantages of the present invention will become more apparent by describing in detail exemplary embodiments thereof with reference to the attached drawings in which:

FIG. 1 is a diagram of the structure of an organic light-emitting device according to an embodiment of the present invention.

DETAILED DESCRIPTION OF THE INVENTION

Organic light-emitting devices manufactured using anthracene derivatives, for example, a compound of phenylanthracene dimer or trimer, as organic emission layer materials are widely known. However, such organic light-emitting devices have a narrow energy gap and lower blue-light color purity since two or three anthracene compounds are linked by conjugation.

In addition, such compounds are highly vulnerable to oxidation and thus are liable to produce impurities, necessitating purification. In order to overcome these drawbacks, organic light-emitting devices manufactured using an anthracene compound including naphthalene groups at 1,9 positions of anthracene or using a diphenylanthracene compound including an aryl group at m-position of the phenyl group have been introduced. However, these organic light-emitting devices have a lower light-emission efficiency.

Organic light-emitting devices may also be manufactured using naphthalene-substituted monoanthracene derivatives. However, the light-emission efficiency thereof is low at about 1 cd/A, and thus such organic light-emitting devices are not suitable for practical use. Furthermore, organic light-emitting devices may be manufactured using phenylanthracene compounds including aryl substituents at m-position. Such compounds have good thermal resistance but lead to an unsatisfactorily low light-emission efficiency of about 2 cd/A, and thus further improvement is required in this regard.

The present invention will now be described more fully with reference to the accompanying drawings, in which exemplary embodiments of the invention are shown.

According to an embodiment of the present invention, a heterocyclic compound is represented by Formula 1 below:

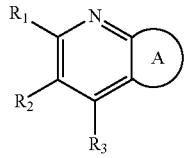

Formula 1

In Formula 1, $R_1$ to $R_3$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, an amino group substituted with a $C_5$-$C_{60}$ aryl group or a $C_3$-$C_{60}$ heteroaryl group, a substituted or unsubstituted $C_3$-$C_{60}$ heteroaryl group, a substituted or unsubstituted $C_6$-$C_{60}$ fused polycyclic group, a halogen atom, a cyano group, a nitro group, a hydroxyl group, or a carboxyl group.

According to another embodiment of the present invention, a heterocyclic compound is represented by Formula 2 or 3 below:

Formula 2

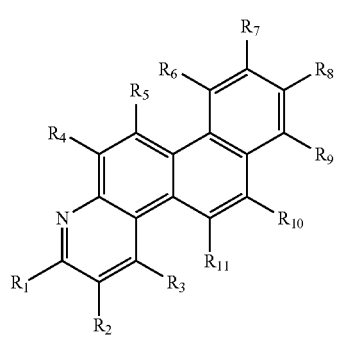

Formula 3

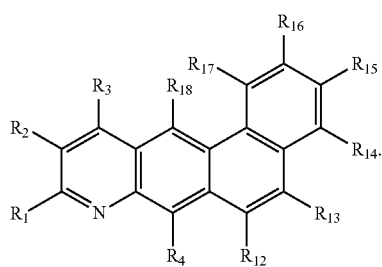

In Formulae 2 and 3, $R_1$ to $R_{18}$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, an amino group substituted with a $C_5$-$C_{60}$ aryl group or a $C_3$-$C_{60}$ heteroaryl group, a substituted or unsubstituted $C_3$-$C_{60}$ heteroaryl group, a substituted or unsubstituted $C_6$-$C_{60}$ fused polycyclic group, a halogen atom, a cyano group, a nitro group, a hydroxyl group, or a carboxyl group.

The heterocyclic compound of Formula 1, 2 or 3 may be used as a light-emitting material, an electron-transporting material or an electron-injecting material. The heterocyclic compound of Formula 1, 2 or 3, having a heterocyclic group in the molecules thereof, has a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments.

An organic light-emitting device manufactured using the heterocyclic compound of Formula 1, 2 or 3 has high durability when stored or operated.

Substituents in Formulae 1 to 3 will now be described in detail.

According to an embodiment of the present invention, in Formulae 2 and 3, $R_1$ to $R_{18}$ may be each independently a hydrogen atom, a deuterium atom, a cyano group, a halogen atom, a substituted or unsubstituted $C_1$-$C_{20}$ alkyl group, a substituted or unsubstituted $C_5$-$C_{40}$ aryl group, a substituted or unsubstituted $C_3$-$C_{40}$ heteroaryl group, an amino group substituted with a $C_5$-$C_{40}$ aryl group or a $C_3$-$C_{20}$ heteroaryl group, or a substituted or unsubstituted $C_6$-$C_{40}$ fused polycyclic group.

According to another embodiment of the present invention, in Formulae 2 and 3, $R_1$ to $R_{18}$ may be each independently a hydrogen atom, a deuterium atom, a halogen atom, a cyano group, a substituted or unsubstituted $C_1$-$C_{20}$ alkyl group, or groups represented by Formulae 2a to 2g below:

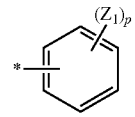
2a

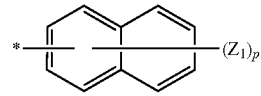
2b

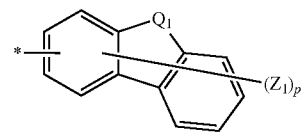
2c

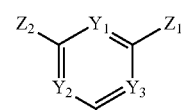
2d

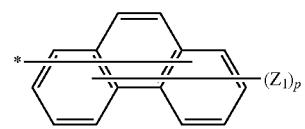
2e

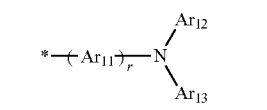
2f

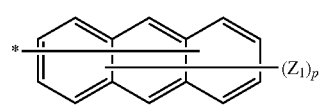
2g

In Formulae 2a to 2g, $Q_1$ is a linking group selected from among —C($R_{19}$)($R_{20}$)—, —N($R_{21}$)—, —S— and —O—; $Y_1$, $Y_2$ and $Y_3$ are each independently a linking group selected from among —N═ and —C($R_{22}$)═; $Z_1$, $Z_2$, $Ar_{12}$, $Ar_{13}$, $R_{19}$, $R_{20}$, $R_{21}$ and $R_{22}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; $Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group; p is an integer from 1 to 7; r is an integer from 0 to 5; and * indicates a binding site.

According to another embodiment of the present invention, in Formulae 2 and 3, $R_1$ to $R_{18}$ may be each independently a hydrogen atom, a deuterium atom, a halogen atom, a cyano group, a methyl group, an ethyl group, a propyl group, a butyl group, a pentyl group, or groups represented by Formulae 3a to 3c below:

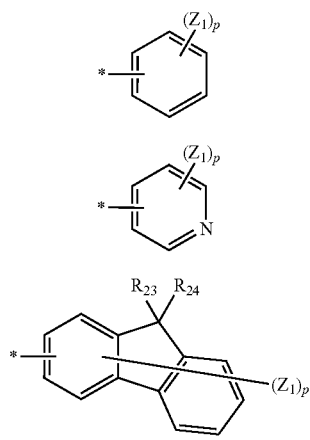

In Formulae 3a to 3c above, $Z_1$, $R_{23}$ and $R_{24}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; p is an integer from 1 to 7; and * indicates a binding site.

According to another embodiment of the present invention, in Formulae 2 and 3, $R_1$, $R_2$, $R_3$, $R_5$, $R_6$, $R_7$, $R_8$, $R_9$, $R_{11}$, $R_{12}$, $R_{14}$, $R_{15}$, $R_{16}$, $R_{17}$ and $R_{18}$ may be each independently a hydrogen atom or a deuterium atom.

According to another embodiment of the present invention, in Formulae 2 and 3, $R_1$, $R_2$, $R_3$, $R_5$, $R_6$, $R_7$, $R_8$, $R_9$, $R_{11}$, $R_{12}$, $R_{14}$, $R_{15}$, $R_{16}$, $R_{17}$ and $R_{18}$ may be each independently a hydrogen atom or a deuterium atom, and $R_4$, $R_{10}$ and $R_{13}$ are each independently a hydrogen atom, a deuterium atom, a halogen atom, a cyano group, a substituted or unsubstituted $C_1$-$C_{20}$ alkyl group, or groups represented by Formulae 2a to 2g below:

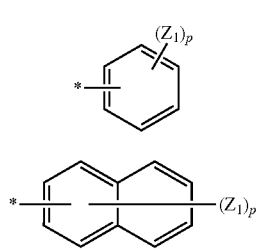

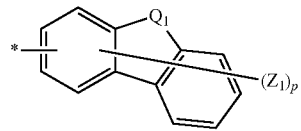

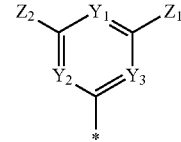

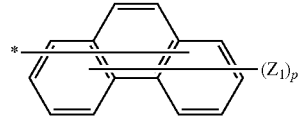

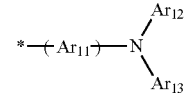

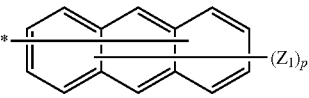

In Formulae 2a to 2g, $Q_1$ is a linking group selected from among —$C(R_{19})(R_{20})$—, —$N(R_{21})$—, S— and —O—; $Y_1$, $Y_2$ and $Y_3$ are each independently a linking group selected from among —N═ and $C(R_{22})$═; $Z_1$, $Z_2$, $Ar_{12}$, $Ar_{13}$, $R_{19}$, $R_{20}$, $R_{21}$ and $R_{22}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; $Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group; p is an integer from 1 to 7; r is an integer from 0 to 5; and * indicates a binding site.

According to another embodiment of the present invention, in Formulae 2 and 3, $R_1$, $R_2$, $R_3$, $R_5$, $R_6$, $R_7$, $R_8$, $R_9$, $R_{11}$, $R_{12}$, $R_{14}$, $R_{15}$, $R_{16}$, $R_{17}$ and $R_{18}$ may be each independently a hydrogen atom and a deuterium atom, and $R_4$, $R_{10}$ and $R_{13}$ may be each independently a hydrogen atom, a deuterium atom, a halogen atom, a cyano group, a methyl group, an ethyl group, a propyl group, a butyl group, a pentyl group, or groups represented by Formulae 3a to 3c below:

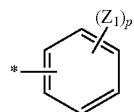

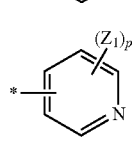

-continued

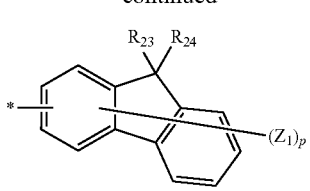
3c

In Formulae 3a to 3c above, $Z_1$, $R_{23}$ and $R_{24}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; p is an integer from 1 to 7; and * indicates a binding site.

Hereinafter, substituents described with reference to the above-described Formulae will now be described in detail. In this regard, the numbers of carbons in substituents are presented only for illustrative purposes and do not limit the characteristics of the substituents.

As used herein, the term "unsubstituted $C_1$-$C_{60}$ alkyl group" may have a linear or branched group. Examples of the unsubstituted $C_1$-$C_{60}$ alkyl group include, but are not limited to, methyl, ethyl, propyl, isobutyl, sec-butyl, pentyl, iso-amyl, hexyl, heptyl, octyl, nonanyl, dodecyl, and the like. At least one hydrogen atom of the unsubstituted $C_1$-$C_{60}$ alkyl group may be substituted with a deuterium atom, a halogen atom, a hydroxy group, a nitro group, a cyano group, an amino group, an amidino group, hydrazine, hydrazone, a carboxyl group or a salt thereof, a sulfone acid or a salt thereof, phosphoric acid or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

In the above-described Formulae, the unsubstituted $C_2$-$C_{60}$ alkenyl group indicates a hydrocarbon chain having at least one carbon-carbon double bond in the center or at a terminal of the unsubstituted $C_2$-$C_{60}$ alkyl group. Non-limiting examples of the unsubstituted $C_2$-$C_{60}$ alkenyl group include ethenyl, propenyl, and butenyl. At least one hydrogen atom of the unsubstituted $C_2$-$C_{60}$ alkenyl group may be substituted with the substituents as those described above in conjunction with the unsubstituted $C_1$-$C_{60}$ alkyl group.

As used herein, the unsubstituted $C_2$-$C_{60}$ alkynyl group indicates a hydrocarbon chain having at least one carbon-carbon triple bond in the center or at a terminal of the unsubstituted $C_2$-$C_{60}$ alkyl group. An example of the unsubstituted $C_2$-$C_{60}$ alkynyl group is acetylenyl, propylene, phenylacetylene, naphacetylene, isopropylacetylene, t-butylacetylene, and diphenylacetylene. At least one hydrogen atom of the unsubstituted $C_2$-$C_{60}$ alkynyl group may be substituted with the substituents as those described above in conjunction with the unsubstituted $C_1$-$C_{60}$ alkyl group.

As used herein, the unsubstituted $C_3$-$C_{60}$ cycloalkyl group indicates a $C_3$-$C_{60}$ alkyl group having a ring shape. At least one hydrogen atom of the unsubstituted $C_3$-$C_{60}$ cycloalkyl group may be substituted with the substituents as those described above in conjunction with the unsubstituted $C_1$-$C_{60}$ alkyl group.

As used herein, the unsubstituted $C_1$-$C_{60}$ alkoxy group refers to a group having a structure of —OA wherein A is an unsubstituted $C_1$-$C_{60}$ alkyl group as described above. Examples of the unsubstituted $C_1$-$C_{60}$ alkoxy group include a methoxy group, an ethoxy group, a propoxy group, an iso-propyloxy group, a butoxy group, and a pentoxy group. At least one hydrogen atom of the unsubstituted $C_1$-$C_{60}$ alkoxy group may be substituted with the substituents as those described above in conjunction with the unsubstituted $C_1$-$C_{60}$ alkyl group.

As used herein, the unsubstituted $C_5$-$C_{60}$ aryl group indicates an unsubstituted $C_5$-$C_{60}$ carbocyclic aromatic system having at least one ring. When the unsubstituted $C_5$-$C_{60}$ aryl group has at least two rings, the rings may be fused to each other, or may be connected through single bond, and the like. The term 'aryl group' includes an aromatic system such as phenyl, naphthyl, anthracenyl. In addition, at least one hydrogen atom of the unsubstituted $C_5$-$C_{60}$ aryl group may be substituted with the substituents as those described above in conjunction with the unsubstituted $C_1$-$C_{60}$ alkyl group.

Examples of the substituted or unsubstituted $C_5$-$C_{60}$ aryl group include a phenyl group, a $C_1$-$C_{10}$ alkylphenyl group (e.g., an ethylphenyl group), a halophenyl group (e.g., an o-, m- or p-fluorophenyl group and a dichlorophenyl group), a dicyanophenyl group, a cyanophenyl group, a trifluoromethoxyphenyl group, a biphenyl group, a halobiphenyl group, a cyanobiphenyl group, a $C_1$-$C_{10}$ alkylbiphenyl group, a $C_1$-$C_{10}$ alkoxybiphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group.

As used herein, the unsubstituted $C_3$-$C_{60}$ heteroaryl group includes one, two or three hetero atoms selected from nitrogen (N), oxygen (O), phosphorus (P), or sulfur (S). When the unsubstituted $C_3$-$C_{60}$ heteroaryl group includes two rings or more, the rings may be fused, or may be connected through single bond. Examples of the unsubstituted $C_4$-$C_{60}$ heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and dibenzothiophene group. At least one hydrogen atom of the unsubstituted $C_4$-$C_{60}$ heteroaryl group may be substituted with the substituents as those described above in conjunction with the unsubstituted $C_1$-$C_{60}$ alkyl group.

As used herein, the unsubstituted $C_5$-$C_{60}$ aryloxy group is —$OA_1$, wherein $A_1$ is a $C_5$-$C_{60}$ aryl group. Examples of the unsubstituted $C_5$-$C_{60}$ aryloxy group may include phenoxy, or the like. At least one hydrogen atom of the unsubstituted $C_5$-$C_{60}$ aryloxy group may be substituted with the substituents as those described above in conjunction with the unsubstituted $C_1$-$C_{60}$ alkyl group.

As used herein, the unsubstituted $C_5$-$C_{60}$ arylthio group is —$SA_1$, wherein $A_1$ is a $C_5$-$C_{60}$ aryl group. Examples of the unsubstituted $C_5$-$C_{60}$ arylthio group may include benzenethio group, a naphthylthio group, or the like. At least one hydrogen atom of the unsubstituted $C_5$-$C_{60}$ arylthio group may be substituted with the substituents as those described above in conjunction with the unsubstituted $C_1$-$C_{60}$ alkyl group.

As used herein, the unsubstituted $C_6$-$C_{60}$ fused polycyclic group is a substituent including two or more rings formed by fusing at least one aromatic ring and at least one non-aromatic ring or a substituent that includes an unsaturated group, but not a conjugated structure, in a ring. The unsubstituted $C_6$-$C_{60}$ fused polycyclic group is different from an aryl group or a heteroaryl group in that the fused polycyclic group does not have aromaticity overall.

Examples of the compound represented by Formula 2 or 3 may include Compounds 1 through 49. However, the compound represented by Formulae 2 and 3 are not limited thereto.

1

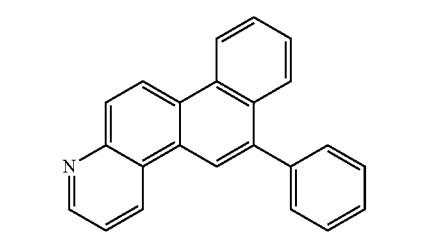

2

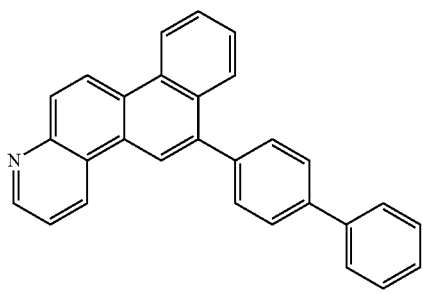

3

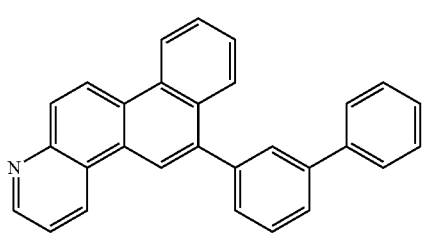

4

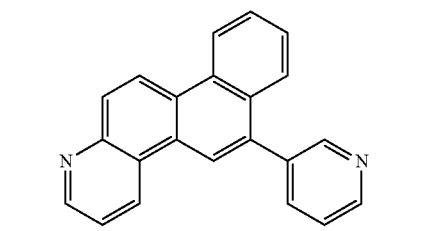

-continued

5

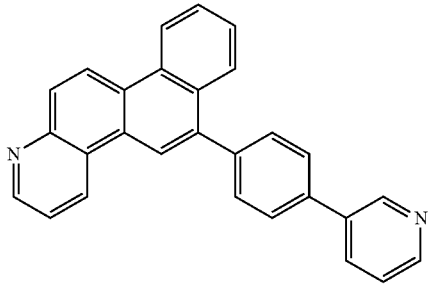

6

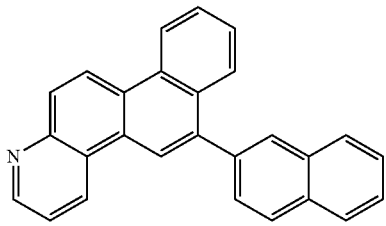

7

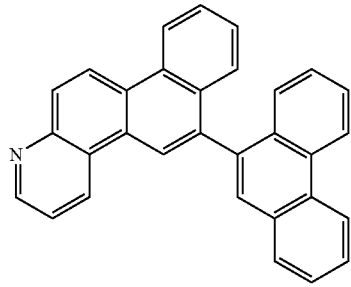

8

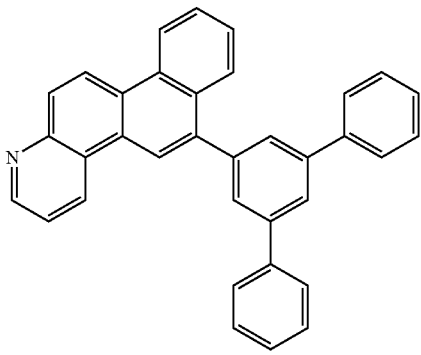

9

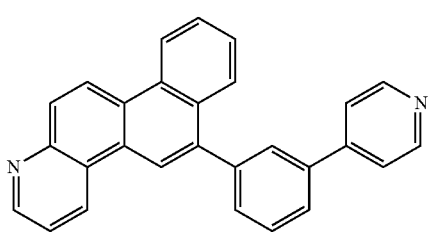

10
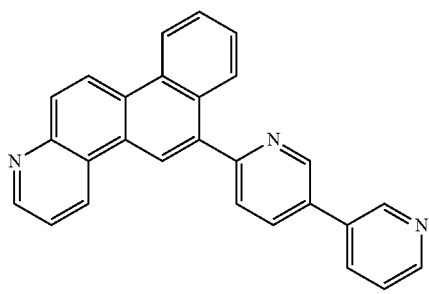
11
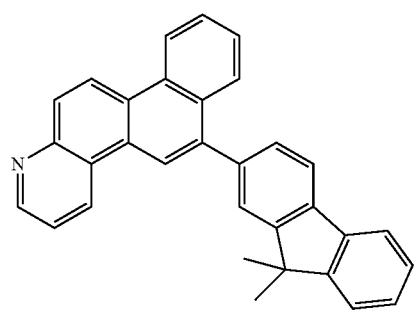
12
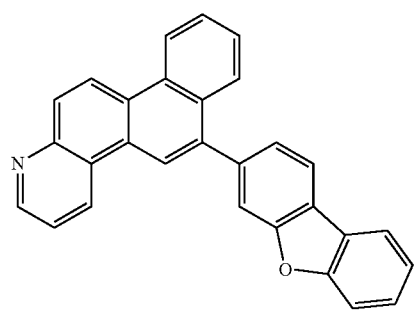
13
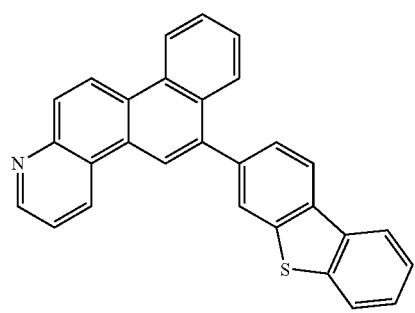
14
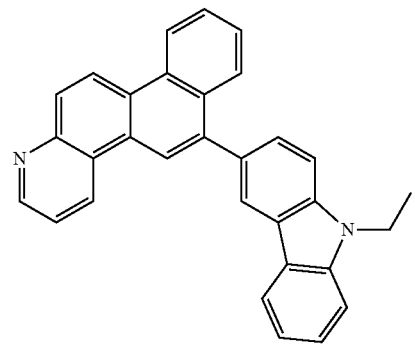
15
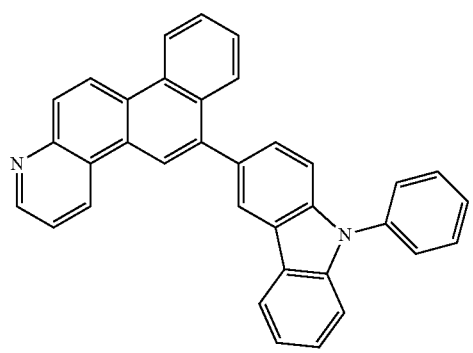
16
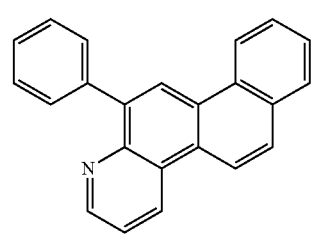
17
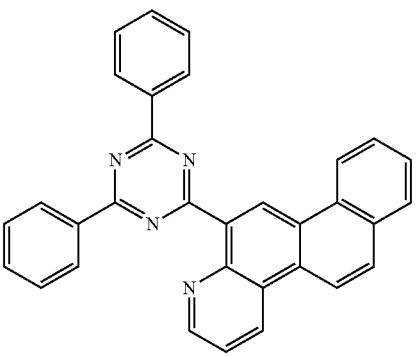
18
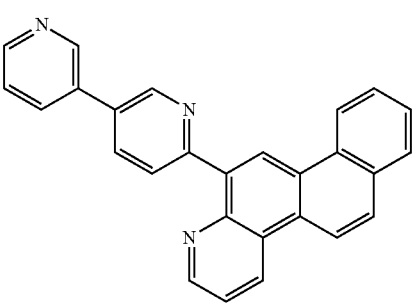
19
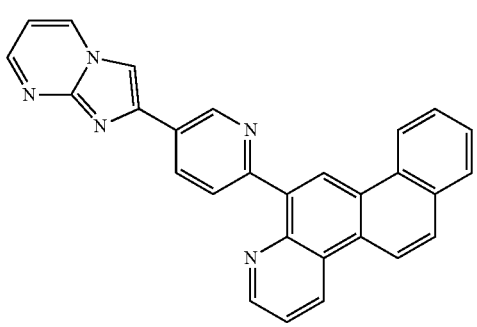

20
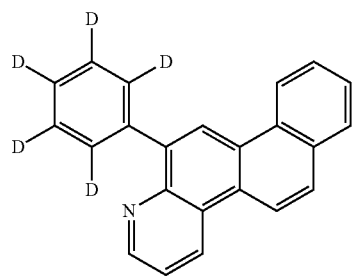
21
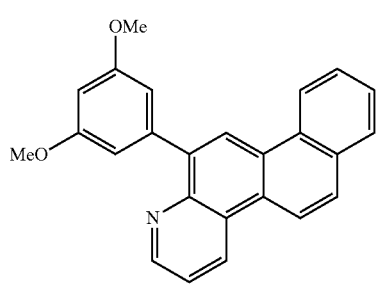
22
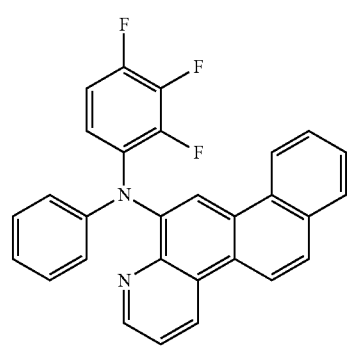
23
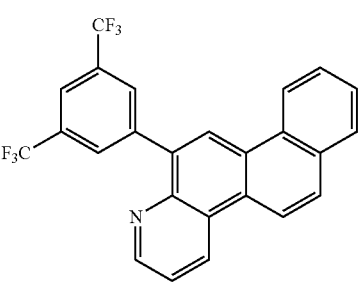
24
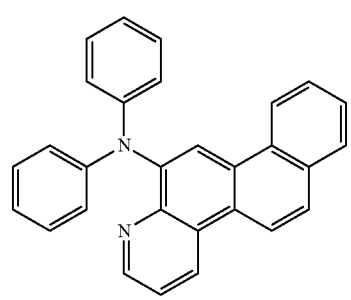
25
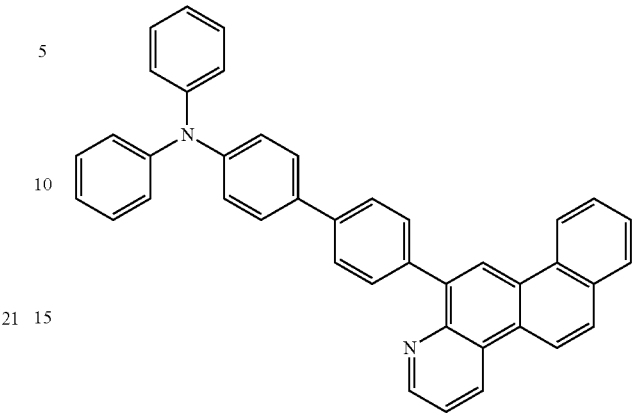
26
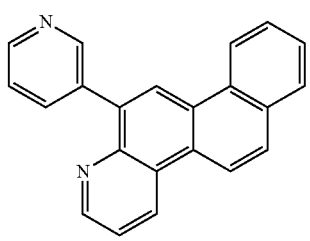
27
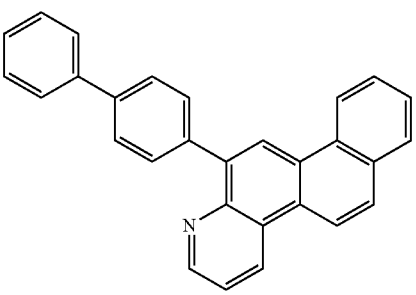
28
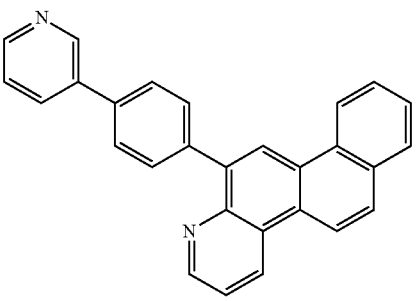
29
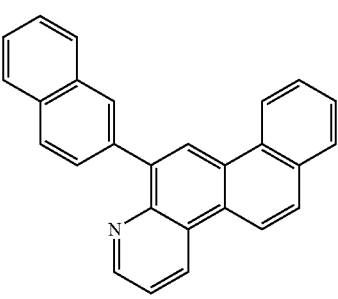

-continued
30
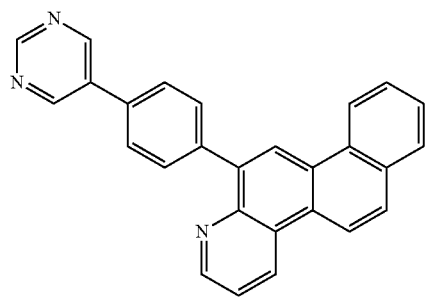
31
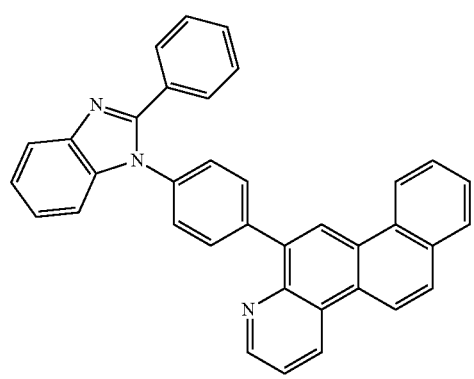
32
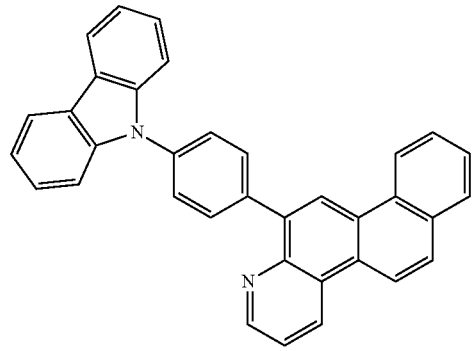
33
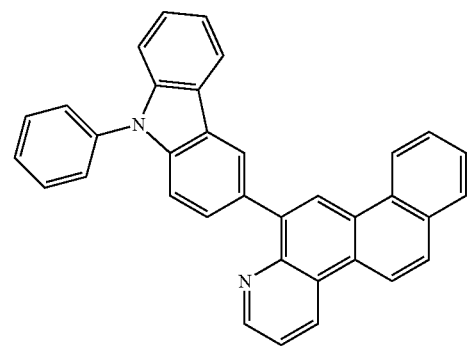
-continued
34
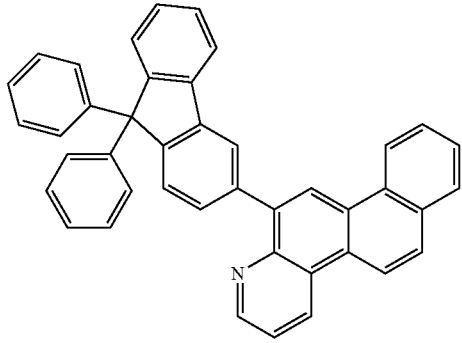
35
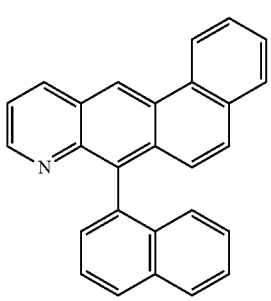
36
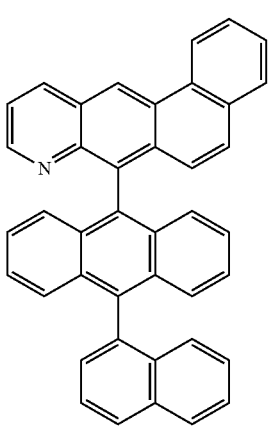
37
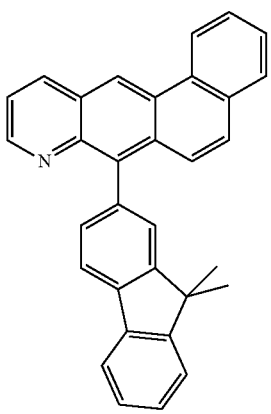

23
-continued
38
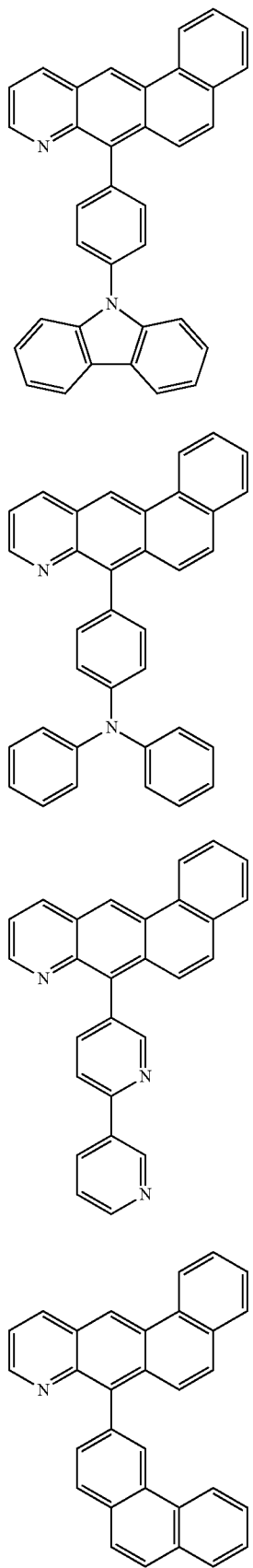
39
40
41
24
-continued
42
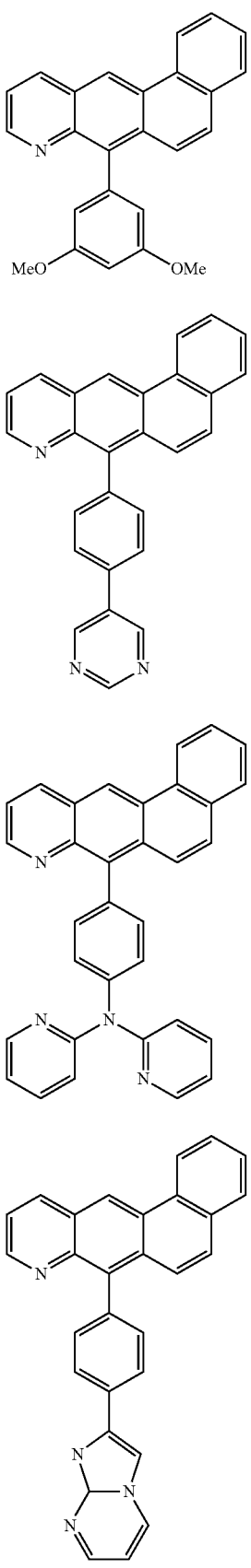
43
44
45

-continued

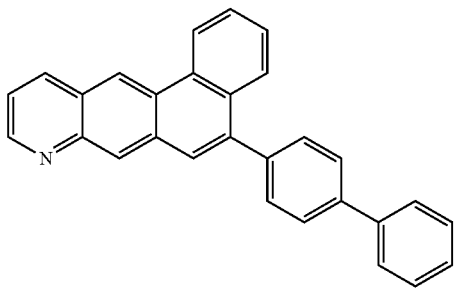
46

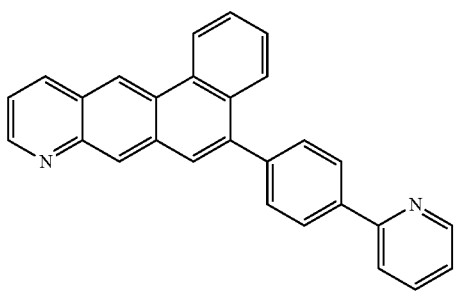
47

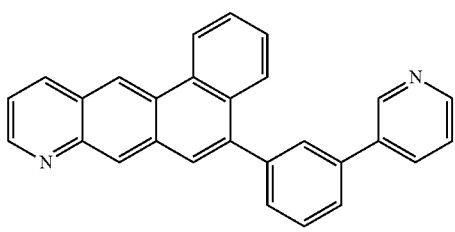
48

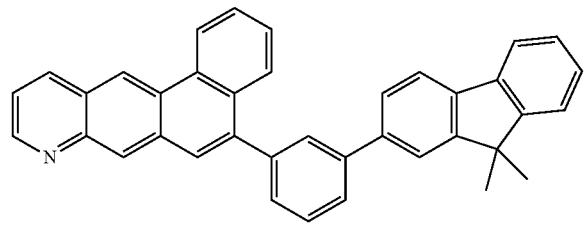
49

According to an embodiment of the present invention, an organic light-emitting device includes a first electrode; a second electrode; and an organic layer interposed between the first electrode and the second electrode, wherein the organic layer includes a first layer including the above-described heterocyclic compound.

The first layer including the above-described heterocyclic compound may be a hole injection layer (HIL), a hole transport layer (HTL), a layer having both a hole injection function and a hole transport function, an electron injection layer (EIL), an electron transport layer (ETL), or a layer having both an electron injection function and an electron transport function.

According to an embodiment of the present invention, the first layer may include an HIL, an HTL, a layer having both a hole injection function and a hole transport function, an EIL, an ETL, or a layer having both an electron injection function and an electron transport function, and may further include a charge-generating material.

The charge-generating material will be described later.

According to an embodiment of the present invention, the first layer may be an EML, may include the above-described heterocyclic compound as a host or a dopant, may further include an anthracene compound, an arylamine compound or a styryl compound, or may include a red layer, a green layer, a blue layer, or a white layer, which includes a phosphorescence compound.

At least one hydrogen atom of the anthracene compound, the arylamine compound, or the styryl compound may be substituted with the substituents as those described above in conjunction with the unsubstituted $C_1$-$C_{50}$ alkyl group.

The arylamine compound is a $C_1$-$C_{50}$ arylamine group.

According to an embodiment of the present invention, the first layer may be a blue emission layer, and the heterocyclic compound may be used as a blue dopant.

According to an embodiment of the present invention, the organic layer of the organic light-emitting device may further include an HIL, an HTL, a layer having both a hole injection function and a hole transport function, an emission layer (EML), a hole block layer (HBL), an ETL, an EIL, or a combination of at least two thereof, but is not limited thereto. At least one of the HIL, the HTL, and the layer having both a hole injection function and a hole transport function, may further include a charge-generating material in addition to the heterocyclic compound, known hole injecting materials, and known hole transporting materials, in order to improve conductivity of the layers. The EML may include a host and a dopant. The dopant may include a fluorescent dopant or a phosphorescent dopant. The phosphorescent dopant may include Ir, Pt, Os, Re, Ti, Zr, Hf, or any combination of at least two thereof.

The charge-generating material may be a p-dopant. Examples of the p-dopant include a quinone derivative such as tetracyanoquinonedimethane (TCNQ) and 2,3,5,6-tetrafluorotetracyano-1,4-benzoquinonedimethane (F4TCNQ); a metal oxide such as tungsten oxide and molybdenum oxide; and a cyano group-containing compound such as Compound 100 below, but are not limited thereto.

Compound 100

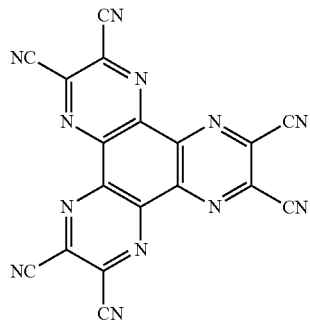

If the HIL, the HTL, or the layer having both hole injecting and hole transporting functions further includes the charge-generating material, the charge-generating material may be homogeneously or non-homogeneously dispersed between the layers, and thus may be changed in various ways.

The ETL of the organic light-emitting device may include an electron transporting organic compound and a metal-containing material. Examples of the electron transporting organic compound may include 9,10-di(naphthalene-2-yl) anthracene (ADN); and anthracene compound that is Compound 101 or 102 below, but are not limited thereto.

Compound 101

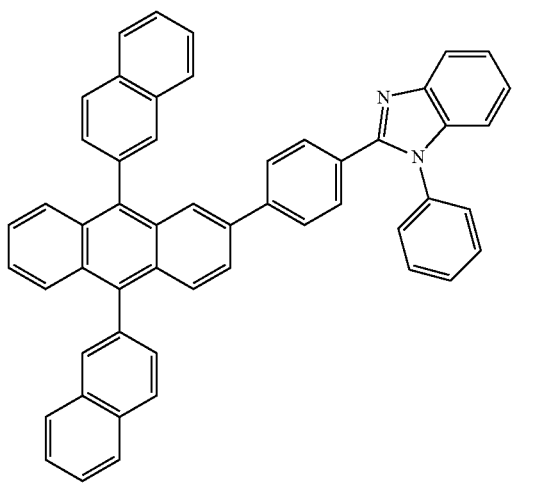

Compound 102

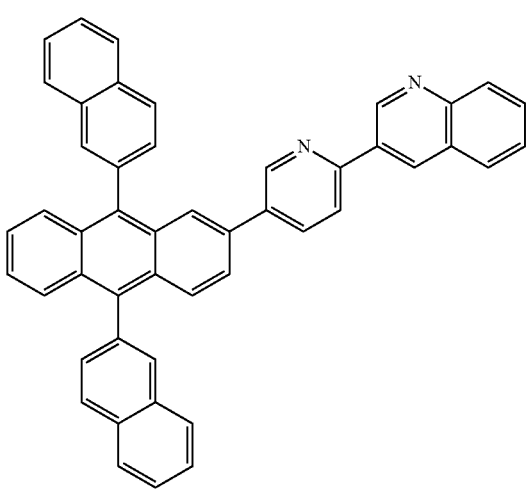

The metal-containing material may include a Li complex. Examples of the Li complex include lithium quinolate (LiQ) or Compound 103 below, but are not limited thereto.

Compound 103

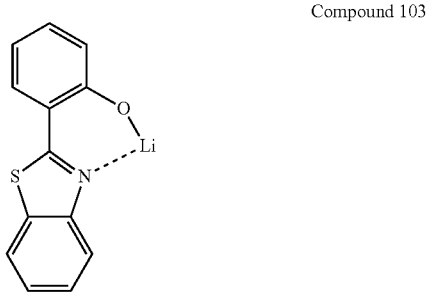

The first electrode may be an anode, and the second electrode may be a cathode, or vice versa.

For example, according to an embodiment of the present invention, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. Alternatively, the organic light-emitting device may have a first electrode/layer having both hole injection and hole transport capabilities/emission layer/electron transport layer/second electrode structure, or a first electrode/layer having both hole injection and hole transport capabilities/emission layer/electron transport layer/electron injection layer/second electrode structure. Alternatively, the organic light-emitting device may have a first electrode/hole transport layer/emission layer/layer having both electron injection and electron transport capabilities/second electrode structure, a first electrode/hole injection layer/emission layer/layer having both electron injection and electron transport capabilities/second electrode structure, or a first electrode/hole injection layer/hole transport layer/emission layer/layer having both electron injection and electron transport capabilities/second electrode structure.

According to an embodiment of the present invention, the organic light-emitting device may be either a top-emission organic light-emitting device or a bottom-emission organic light-emitting device.

Hereinafter, a method of manufacturing an organic light-emitting device according to an embodiment of the present invention will be described with reference to FIG. 1. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

The first electrode may be formed by depositing or sputtering a first electrode-forming material on the substrate. The first electrode may be an anode or a cathode. The substrate may be any substrate that is used in conventional organic light emitting devices. In some embodiments the substrate may be a glass substrate or a transparent plastic substrate with strong mechanical strength, thermal stability, transparency, surface smoothness, ease of handling, and water resistance. The first electrode may be formed of a material with excellent conductivity, such as indium tin oxide (ITO), indium zinc oxide (IZO), $SnO_2$, ZnO, aluminium (Al), silver (Ag), magnesium (Mg), and the like. The first electrode may be formed as a transparent electrode or a reflective electrode.

Next, the HIL may be formed on the first electrode by using any of a variety of methods such as vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec.

When the HIL is formed using spin coating, the coating conditions may vary according to the compound that is used to form the HIL, and the desired structure and thermal properties of the HIL to be formed. For example, the coating rate may be in the range of about 2,000 rpm to about 5,000 rpm, and a temperature at which heat treatment is performed to remove a solvent after coating may be in the range of about 80° C. to about 200° C.

The HIL may be formed of the above-described heterocyclic compound or any hole-injecting material that is known in the art. Non-limiting examples of suitable hole-injecting materials include, a phthalocyanine compound such as copperphthalocyanine, 4,4',4"-tris(3-methylphenylphenylamino)triphenylamine (m-MTDATA), N,N-di(1-naphthyl)-N,N-diphenylbenzidine) (NPB), TDATA, 2T-NATA, polyaniline/Dodecylbenzenesulfonic acid (Pani/DBSA), poly(3,4-ethylenedioxythiophene)/poly(4-styrenesulfonate)

(PEDOT/PSS), polyaniline/Camphor sulfonic acid (Pani/CSA) and polyaniline/Poly(4-styrenesulfonate).

The thickness of the HIL may be from about 100 Å to about 10,000 Å, for example, about 100 Å to about 1,000 Å. When the thickness of the HIL is within these ranges, the HIL may have excellent hole injecting ability without a substantial increase in driving voltage.

Next, the HTL may be formed on the HIL using various methods, for example, vacuum deposition, spin coating, casting, LB deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of the above-described heterocyclic compound or any hole-transporting material that is known in the art. Non-limiting examples of suitable hole-transporting materials include a carbazole derivative such as N-phenylcarbazole or polyvinylcarbazole, and an amine derivative with an aromatic fused ring, such as NPB, or N,N'-bis(3-methylphenyl)-N,N'-diphenyl-[1,1-byphenyl]-4,4'-diamine (TPD).

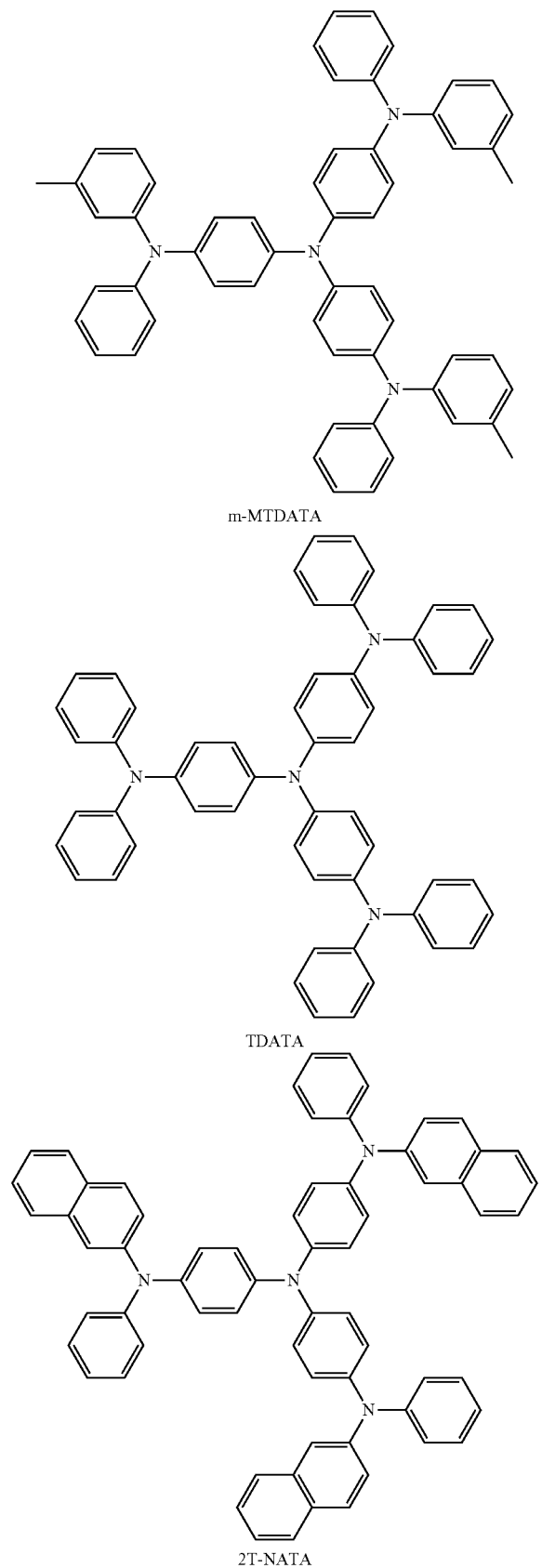

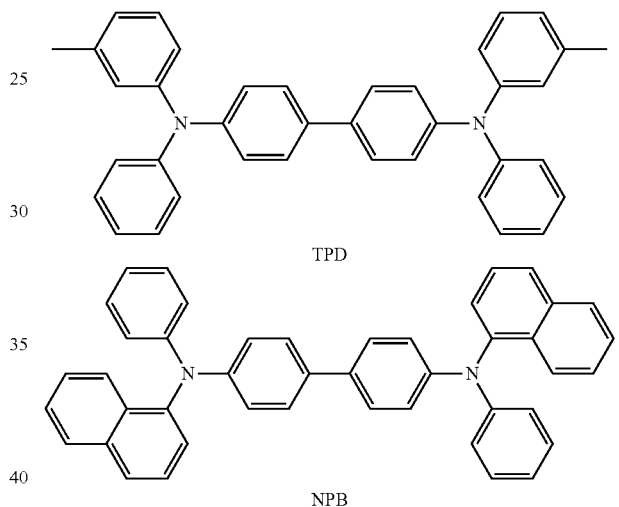

The thickness of the HTL may be from about 50 Å to about 1,000 Å, for example, about 100 Å to about 600 Å. When the thickness of the HTL is within these ranges, the HTL may have excellent hole transporting ability without a substantial increase in driving voltage.

Then, the EML may be formed on the HTL by using vacuum deposition, spin coating, casting, LB deposition, or the like. When the EML is formed using vacuum deposition or spin coating, the deposition and coating conditions may be similar to those for the formation of the HIL, though the conditions for deposition and coating may vary according to the material that is used to form the EML.

The EML may include the above-described heterocyclic compound. For example, the heterocyclic compound represented by Formula 2 or 3 may be used as a host or a dopant. In addition, the EML may be formed of any emitting material that is known in the art, and may be formed by using a host and a dopant that are known in the art. The dopant may be a fluorescence dopant or a phosphate dopant that are known in the art.

Non-limiting examples of the well-known host include tris(8-hydroxyquinoline)aluminum ($Alq_3$), 4,4'-bis(N-carbazolyl)-1,1'-biphenyl (CBP), poly(9-vinylcarbazole) (PVK), 9,10-di(2-naphthyl)anthracene (ADN), tris(4-carbazoyl-9-ylphenyl)amine (TCTA), 1,3,5-tris(N-phenylbenzimidazole-2-yl)benzene (TPBI), 9,10-bis(2-naphthyl)-2-tert-butylanthracene (TBADN), 2,7-bis(9,9-diethylfluorene-2-yl)-9,9-diethylfluorene (E3), and distyrylarylene (DSA).

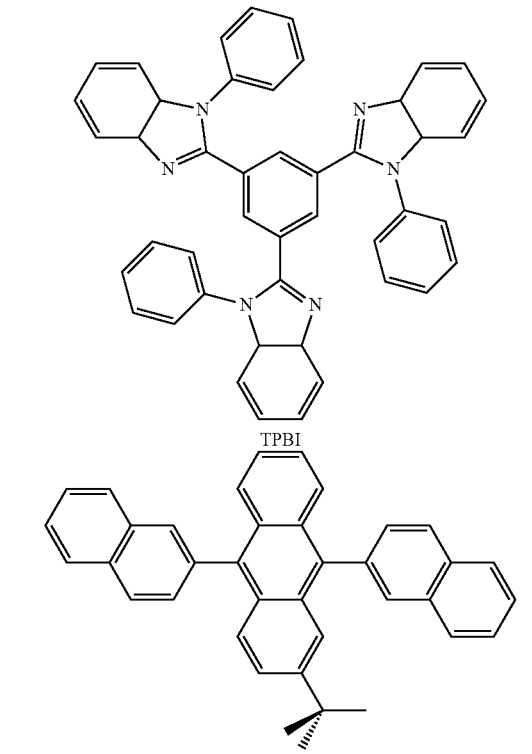
TPBI

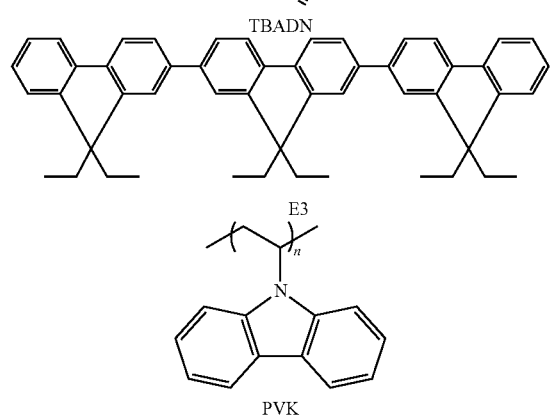
TBADN

E3

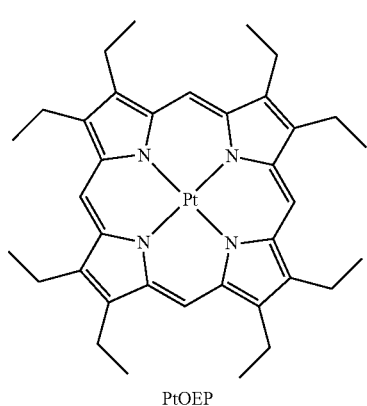
PVK

Meanwhile, examples of known red dopants include PtOEP, Ir(piq)$_3$, Btp$_2$Ir(acac), DCJTB, but are not limited thereto.

PtOEP

-continued

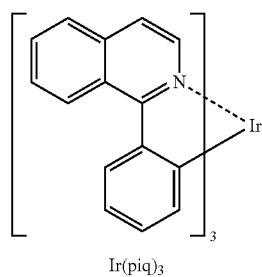
Ir(piq)$_3$

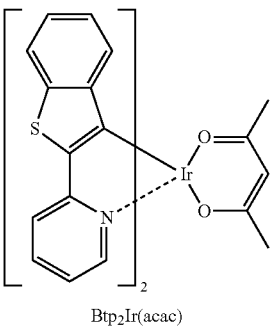
Btp$_2$Ir(acac)

Examples of known green dopants include Ir(ppy)$_3$ (where "ppy" denotes phenylpyridine), Ir(ppy)$_2$(acac), Ir(mpyp)$_3$, and C545T, but are not limited thereto.

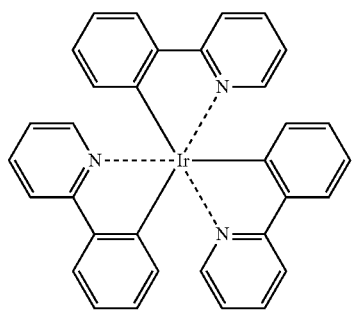
Ir(ppy)$_3$

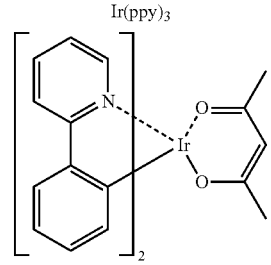
Ir(ppy)$_2$(acac)

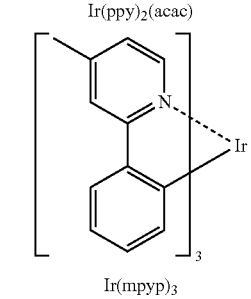
Ir(mpyp)$_3$

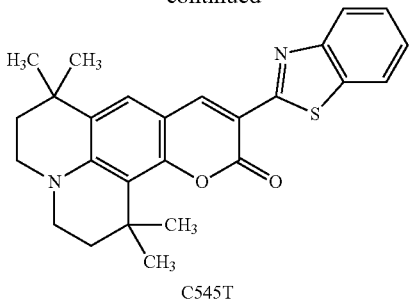

C545T

A blue dopant may be the above-described heterocyclic compound or any well-known blue dopant. Examples of the well-known blue dopant include F$_2$Irpic, (F$_2$ppy)$_2$Ir(tmd), Ir(dfppz)$_3$, ter-fluorene, 4,4'-bis(4-diphenylaminostyryl)biphenyl (DPAVBi), and 2,5,8,11-tetra-t-butyl pherylene (TBP), but are not limited thereto.

be formed on the EML in order to prevent diffusion of triplet excitons or holes into an ETL. Any material that is commonly used to form a HBL may be used. Examples of materials for forming the HBL include an oxadiazole derivative, a triazole derivative, a phenanthroline derivative, Balq, and BCP.

The thickness of the HBL may be in a range of about 50 to about 1,000 Å, for example, about 100 to about 300 Å. When the thickness of the HBL is within theses ranges, the HBL may have good hole blocking characteristics without a substantial increase in driving voltage.

Next, the ETL may be formed by using a method such as vacuum deposition, spin coating, or casting. When the ETL is formed using vacuum deposition or spin coating, the deposition and coating conditions may be similar to those for formation of the HIL, although the deposition and coating conditions may vary according to a compound that is used to form the ETL.

The ETL may be formed of the above-described heterocyclic compound or any well-known material. Examples of the

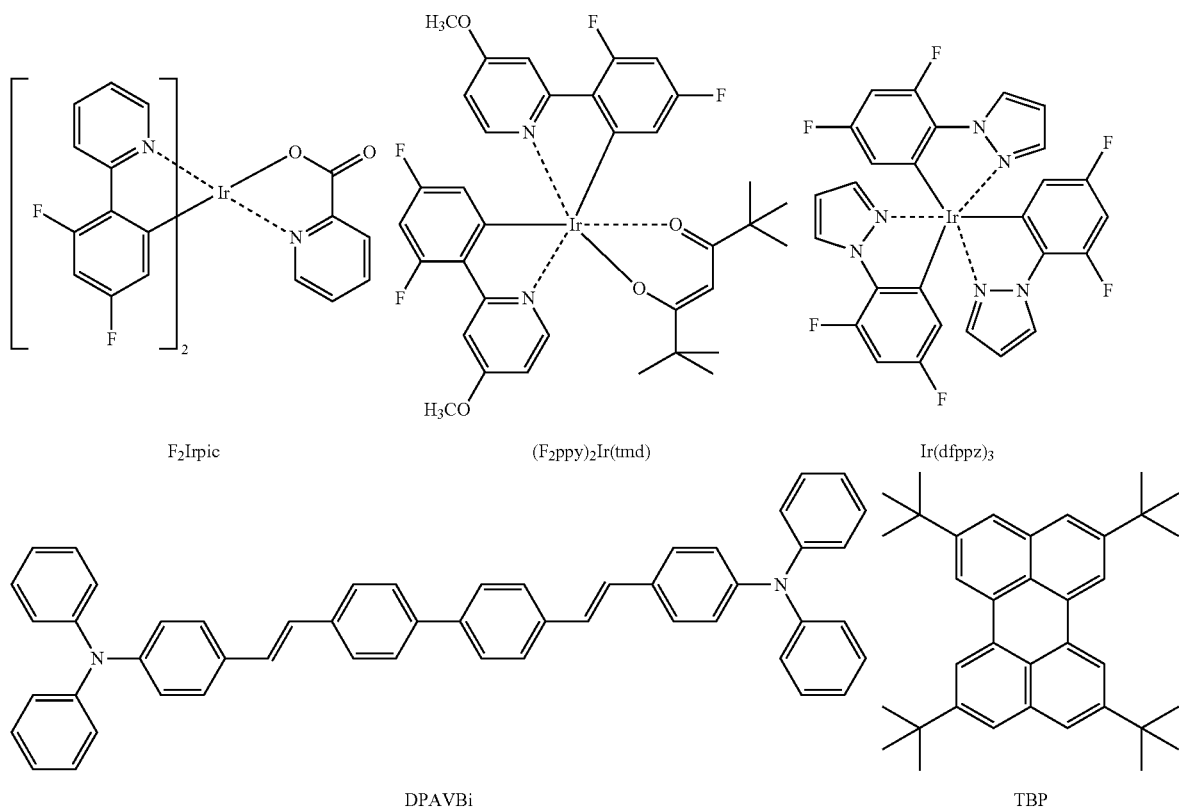

F$_2$Irpic        (F$_2$ppy)$_2$Ir(tmd)        Ir(dfppz)$_3$

DPAVBi        TBP

The amount of the dopant may be in the range of about 0.1 to about 20 parts by weight, for example, about 0.5 to about 12 parts by weight based on 100 parts by weight of the host and the dopant. When the amount of the dopant is within this range, concentration quenching may be substantially prevented.

The thickness of the EML may be in the range of about 100 Å to about 1,000 Å, for example, about 200 Å to about 600 Å. When the thickness of the EML is within this range, the EML may have excellent light emitting ability without a substantial increase in driving voltage.

When a phosphorescent dopant is also used to form the EML, a hole blocking layer (HBL) (not shown in FIG. 1) may ETL material include quinoline derivatives, such as Alq$_3$, TAZ, and beryllium bis(benzoquinolin-10-olate) (Balq$_2$), but are not limited thereto.

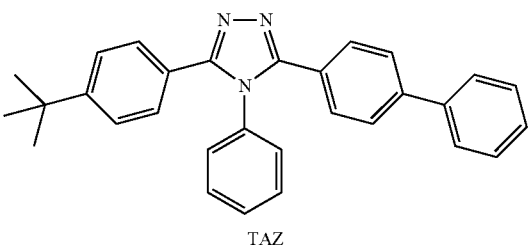

TAZ

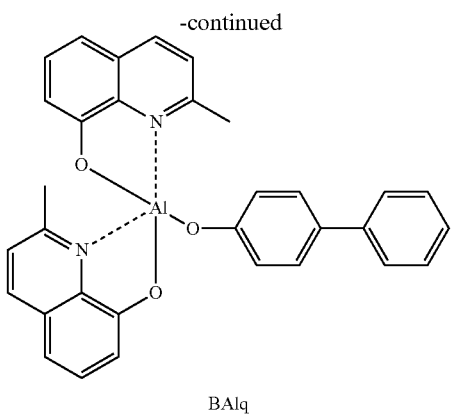

BAlq

The thickness of the ETL may be in the range of about 100 Å to about 1,000 Å, for example, about 150 Å to about 500 Å. When the thickness of the ETL is within the range described above, the ETL may have excellent electron transporting ability without a substantial increase in driving voltage.

Then, an EIL, which facilitates injection of electrons from the cathode, may be formed on the ETL.

Examples of electron-injecting materials for the EIL include the above-described heterocyclic compound, or any electron-injecting material that is known in the art, for example, LiF, NaCl, CsF, $Li_2O$, BaO, or the like. The deposition and coating conditions for forming the EIL may be similar to those for the formation of the HIL, though the deposition and coating conditions may vary according to the material that is used to form the EIL.

The thickness of the EIL may be from about 1 Å to about 100 Å, for example, about 5 Å to about 90 Å. When the thickness of the EIL is within these ranges, the EIL may have satisfactory electron injection ability without a substantial increase in driving voltage.

Lastly, the second electrode may be formed on the EIL by vacuum deposition or sputtering. The second electrode may be a cathode or an anode. The second electrode may be formed of a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may use a transparent cathode formed of indium tin oxide (ITO) or indium zinc oxide (IZO) in order to manufacture a top-emission light-emitting device.

According to embodiments of the present invention, the organic light-emitting device may be included in various types of flat panel display devices, such as in a passive matrix organic light-emitting display device, or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. In addition, the organic light-emitting device may be included in a double-screen flat display device.

According to embodiments of the present invention, the first layer of the organic layers may be formed of the above-described heterocyclic compound by using a deposition method or a wet method of coating a solution of the above-described heterocyclic compound.

Hereinafter, the present invention will be described in detail with reference to the following synthesis examples and other examples of Compounds 18, 19, 22, 32, 37, and 39.

However, these examples are for illustrative purposes only and are not intended to limit the scope of the present invention.

EXAMPLES

Synthesis Example 1

Synthesis of Compound 18

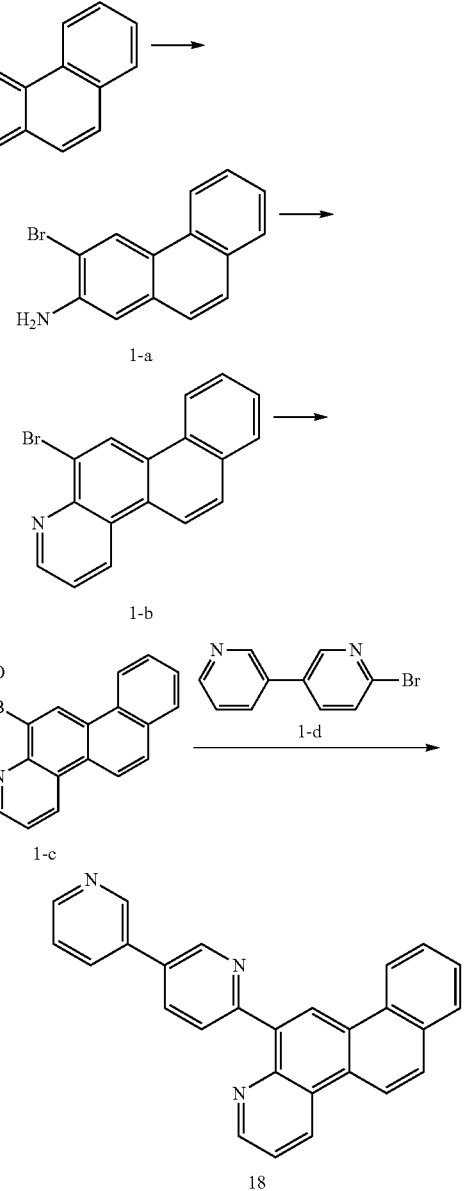

Synthesis of Intermediate 1-a 20 g (103.5 mmol) of 2-aminophenanthrene was dissolved in 100 mL of $CHCl_3$, and 19.8 g (124.2 mmol) of bromine was added thereto. The mixture was stirred at a temperature of 0° C. for 5 hours. The mixture was cooled to room temperature and subjected to extraction two times with 100 mL of saturated $NaHCO_3$ solution and 50 mL of dichloromethane. An organic layer was collected and dried using magnesium sulfate to evaporate the solvent. The residue was separately purified using silica gel column chromatography to obtain 7.04 g of Intermediate 1-a (Yield: 25%).

The produced compound was identified using LC-MS. $C_{14}H_{10}BrN$: M+ 271.00

Synthesis of Intermediate 1-b 7.04 g (25.9 mmol) of Intermediate 1-a and 7 g of a 70% sulfuric acid solution were added to 7 g of nitrobenzene. The mixture was heated to 110° C., and 7 g of glycerol, as an oxidant, was dropwise added thereto. Then, the mixture was stirred at 110° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 6.0 g of Intermediate 1-b (Yield: 75%).

The produced compound was identified using LC-MS. $C_{17}H_{10}BrN$: M+ 307.00

Synthesis of Intermediate 1-c 6 g (19.5 mmol) of Intermediate 1-b, 5.8 g (22.86 mmol) of bis(pinacolato)diboron, 5.7 g (58.5 mmol) of potassium acetate (KOAc), and 0.66 g (1.1 mmol) of 1,1'-bis(diphenylphosphino)ferroceneldichloropalladium(II) (Pd(dppf)Cl$_2$) were mixed with degassed DMF. Then, the mixture was stirred at a temperature of 60° C. for 10 hours. The mixture was cooled to room temperature and subjected to extraction three times with 100 mL of water and 100 mL of dichloromethane. An organic layer was collected and dried using magnesium sulfate to evaporate the solvent. The residue was separately purified using silica gel column chromatography to obtain 6.1 g of Intermediate 1-c (Yield: 88%).

The produced compound was identified using LC-MS. $C_{23}H_{22}BNO_2$: M+ 355.17

Synthesis of Compound 18

1 g (2.8 mmol) of Intermediate 1-c, 0.8 g (3.4 mmol) of Intermediate 1-d, and 0.1 g (0.08 mmol) of tetrakis(triphenylphosphin)palladium (O) (Pd(PPh$_3$)$_4$) were mixed with 10 mL of 2M NaOH solution and 10 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 0.8 g of Compound 18 (Yield: 72%).

The produced compound was identified using LC-MS and NMR. $C_{27}H_{17}N_3$: M+ 383.14

$^1$H NMR (CDCl$_3$, 400 MHz) δ (ppm) 8.91 (s, 1H) 8.58 (m, 1H) 8.48-8.44 (m, 2H) 8.38 (m, 1G) 8.26-8.24 (d, 1H) 8.17-8.14 (m, 2H) 7.95-7.86 (m, 3H) 7.77 (d, 1H) 7.72-7.70 (m, 1H) 7.62-7.52 (m, 21-1) 7.46-7.42 (m, 2H)

Synthesis Example 2

Synthesis of Compound 19

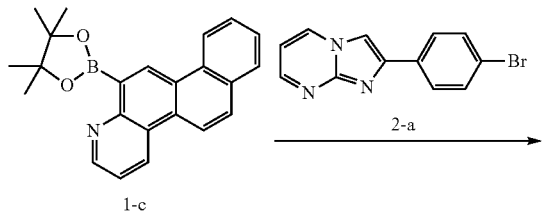

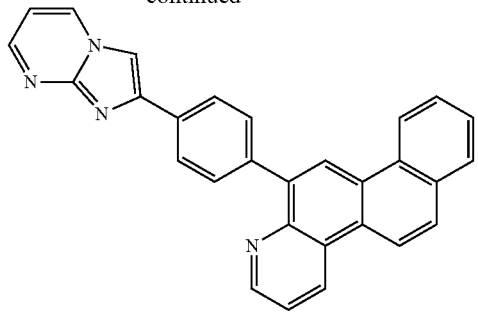

1 g (2.8 mmol) of Intermediate 1-c, 0.93 g (3.4 mmol) of Intermediate 2-a, and 0.1 g (0.08 mmol) of Pd(PPh$_3$)$_4$ were mixed with 10 mL of 2M NaOH solution and 10 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 0.83 g of Compound 19 (Yield: 70%).

The produced compound was identified using LC-MS and NMR. $C_{29}H_{18}N_4$: M+ 422.15

$^1$H NMR (CDCl$_3$, 400 MHz) δ (ppm) 8.92 (s, 1H) 8.81 (d, 1H) 8.65-8.62 (m, 2H) 8.50-8.48 (m, 1H) 8.43-8.38 (m, 2H) 9.31-8.27 (m, 2H) 8.07 (m, 1H) 8.05-8.02 (m, 2H) 7.97 (m, 1H) 7.89 (s, 1H) 7.72-7.62 (m, 2H) 7.38-7.35 (m, 1H) 7.11-7.10 (m, 1H)

Synthesis Example 3

Synthesis of Compound 22

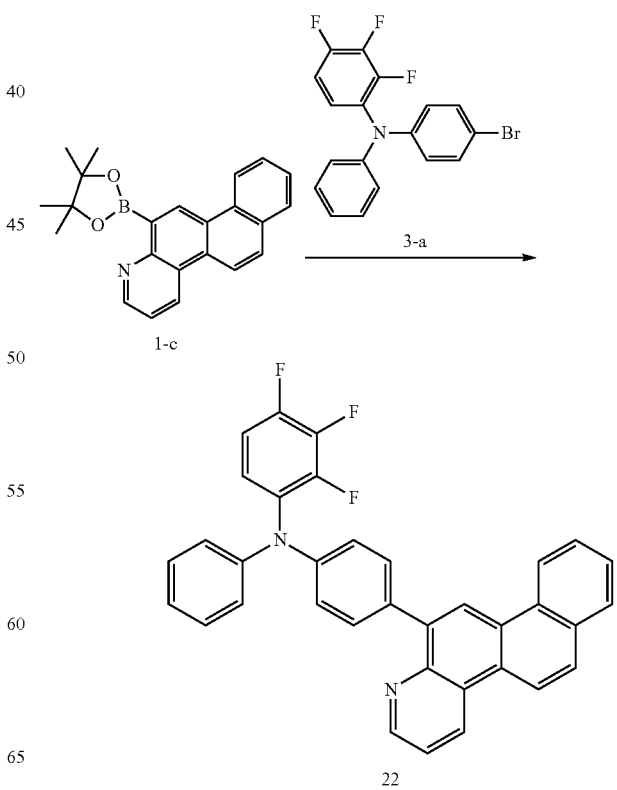

1 g (2.8 mmol) of Intermediate 1-c, 1.3 g (3.4 mmol) of Intermediate 3-a, and 0.1 g (0.08 mmol) of Pd(PPh$_3$)$_4$ were mixed with 10 mL of 2M NaOH solution and 10 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel, column chromatography to obtain 0.96 g of Compound 22 (Yield: 65%).

The produced compound was identified using LC-MS and NMR. $C_{35}H_{21}F_3N_2$: M+ 526.17

$^1$H NMR (CDCl$_3$, 400 MHz) δ (ppm) 8.91 (m, 1H) 8.85 (s, 1H) 8.65-8.62 (m, 2H) 8.40-8.38 (m, 1H) 8.17 (d, 1H) 8.07 (d, 1H) 7.82-7.72 (m, 4H) 7.58-7.55 (m, 1H) 7.44-7.41 (m, 2H) 7.31-7.21 (m, 4H) 7.19-7.11 (m, 1H) 7.03-7.01 (m, 2H)

Synthesis Example 4

Synthesis of Compound 32

1 g (2.8 mmol) of Intermediate 1-c, 1.1 g (3.4 mmol) of Intermediate 4-a, and 0.1 g (0.08 mmol) of Pd(PPh$_3$)$_4$ were mixed with 10 mL of 2M NaOH solution and 10 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 0.98 g of Compound 32 (Yield: 74%).

The produced compound was identified using LC-MS and NMR. $C_{35}H_{22}N_2$: M+ 470.18

$^1$H NMR (CDCl$_3$, 400 MHz) δ (ppm) 8.91 (s, 1H) 8.82-8.80 (m, 1H) 8.65-8.63 (m, 2H) 8.39 (d, 1H) 8.12-8.06 (m, 3H) 7.97 (d, 1H) 7.72-7.62 (m, 4H) 7.38-7.2 (m, 9H)

Synthesis Example 5

Synthesis of Compound 37

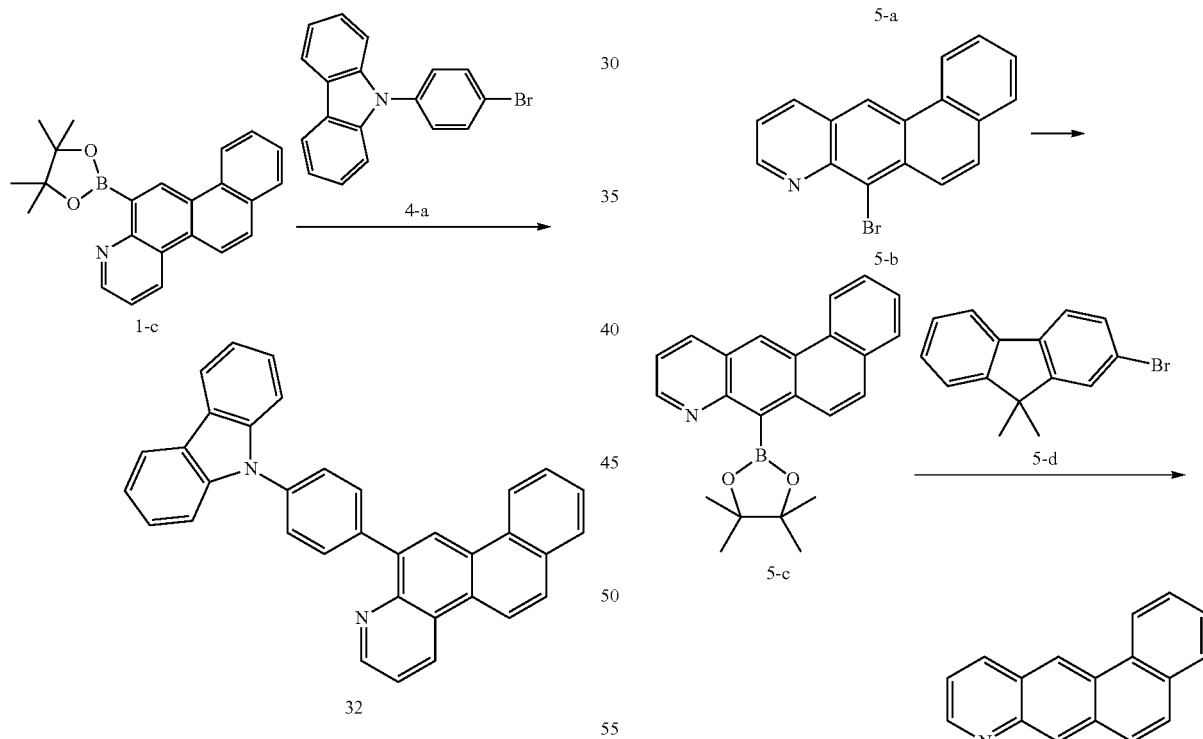

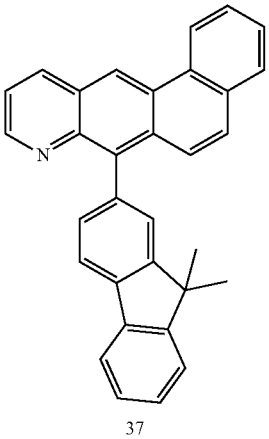

Synthesis of Intermediate 5-a 20 g (103.5 mmol) of 2-aminophenanthrene 20 g was dissolved in 100 mL of $CHCl_3$ and 19.8 g (124.2 mmol) of bromine was added thereto. The mixture was stirred at a temperature of 0° C. for 5 hours. The mixture was warmed to room temperature and subjected to extraction two times with 100 mL of saturated $NaHCO_3$ solution and 50 mL of dichloromethane. An organic layer was collected and dried using magnesium sulfate to evaporate the solvent. The residue was separately purified using silica gel column chromatography to obtain 15.5 g of Intermediate 5-a (Yield: 55%).

The produced compound was identified using LC-MS. $C_{14}H_{10}BrN$: M+ 271.00

Synthesis of Intermediate 5-b 5.0 g (25.9 mmol) of Intermediate 5-a and 5 g of 70% sulfuric acid solution were added to 4 g of nitrobenzene. The mixture was heated to 110° C., and 5 g of glycerol, as an oxidant, was dropwise added thereto. Then, the mixture was stirred at 110° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 5.67 g of Intermediate 5-b (Yield 71%).

The produced compound was identified using LC-MS. $C_{17}H_{10}BrN$: M+ 307.00

Synthesis of Intermediate 5-c 5.67 g (18.4 mmol) of Intermediate 5-b, 5.8 g (22.1 mmol) of bis(pinacolato)diboron, 5.7 g (55.2 mmol) of KOAc, and 0.66 g (1.1 mmol) of $Pd(dppf)Cl_2$ were mixed with degassed DMF. Then, the mixture was stirred at a temperature of 60° C. for 10 hours. The mixture was cooled to room temperature and subjected to extraction three times with 50 mL of water and 50 mL of dichloromethane. An organic layer was collected and dried using magnesium sulfate to evaporate the solvent. The residue was separately purified using silica gel column chromatography to obtain 4.84 g of Intermediate 5-c (Yield: 74%).

The produced compound was identified using LC-MS. $C_{23}H_{22}BNO_2$: M+ 355.17

Synthesis of Intermediate 37

1 g (2.8 mmol) of Intermediate 5-c, 0.93 g (3.4 mmol) of Intermediate 5-d, and 0.1 g (0.08 mmol) of $Pd(PPh_3)_4$ were mixed with 10 mL of 2M NaOH solution and 10 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 0.83 g of Compound 37 (Yield: 70%).

The produced compound was identified using LC-MS and NMR. $C_{32}H_{23}N_1$: M+ 421.18

$^1$H NMR ($CDCl_3$, 400 MHz) δ (ppm) 8.91 (s, 1H) 8.85 (m, 1H) 8.39 (d, 1H) 8.18 (d, 1H) 7.98-7.96 (m, 2H) 7.87-7.79 (m, 3H) 7.73-7.62 (m, 3H) 7.43-7.30 (m, 3H) 7.15-7.09 (m, 2H)

Synthesis Example 6

Synthesis of Compound 39

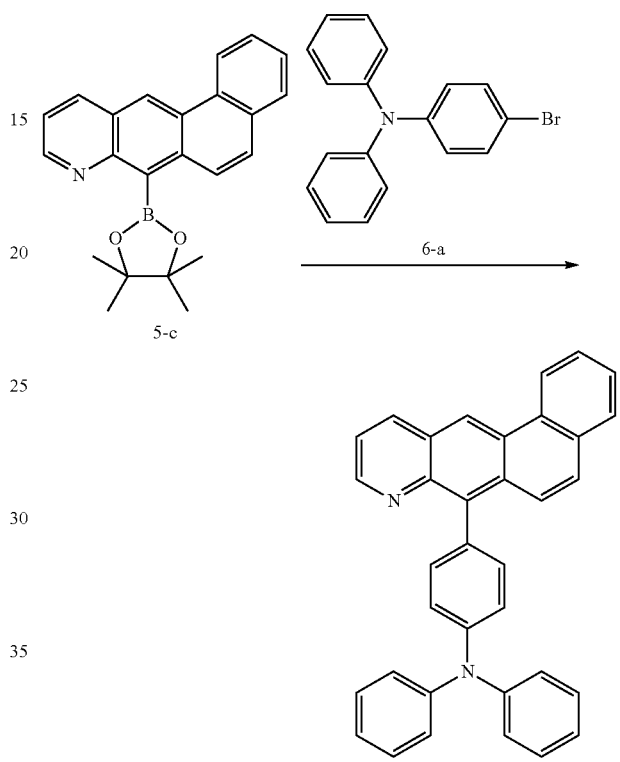

1 g (2.8 mmol) of Intermediate 5-c, 1.1 g (3.4 mmol) of Intermediate 6-a, and 0.1 g (0.08 mmol) of $Pd(PPh_3)_4$ were mixed with 10 mL of 2M NaOH solution and 10 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 0.98 g of Compound 39 (Yield: 74%).

The produced compound was identified using LC-MS and NMR. $C_{35}H_{24}N_2$: M+ 472.19

$^1$H NMR ($CDCl_3$, 400 MHz) δ (ppm) 8.91 (s, 1H) 8.85 (d, 1H) 8.40 (d, 1H) 8.20 (m, 1H) 7.97 (d, 1H) 7.87-7.72 (m, 6H) 7.66-7.63 (m, 1H) 7.56-7.44 (m, 6H) 7.26-7.23 (m, 2H) 7.16-7.12 (m, 4H)

Example 1

To manufacture an anode, a corning 15 Ω/$cm^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

A blue fluorescent host 9,10-di-naphthalene-2-yl-anthracene (ADN) and Compound 22, which is used instead of a blue fluorescent dopant 1,4-bis-(2,2-diphenylvinyl)biphenyl (DPVBi), were deposited at the same time on the HTL in a weight ratio of 98:2 to form an EML having a thickness of 300 Å.

Then, $Alq_3$ was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3,000 Å, thereby forming an LiF/Al electrode and completing the manufacture of an organic light-emitting device.

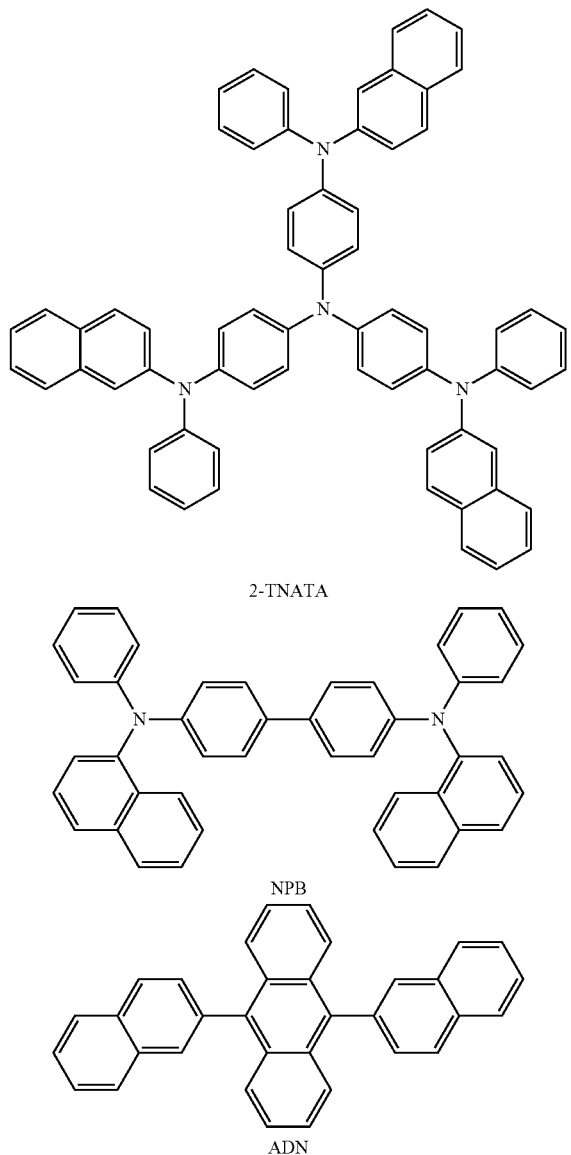

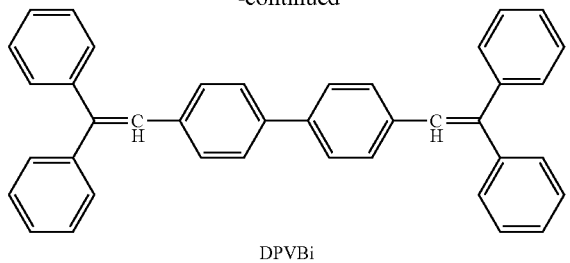

DPVBi

The organic light-emitting device had a driving voltage of 6.59 V at a current density of 50 $mA/cm^2$, a high luminosity of 2395 $cd/m^2$, a luminescent efficiency of 4.97 cd/A, and a half-life span of 172 hours at 100 $mA/cm^2$.

Example 2

An organic light-emitting device was manufactured in the same manner as in Example 1, except that Compound 37 was used instead of Compound 22 to form the EML.

The organic light-emitting device had a driving voltage of 6.71 V at a current density of 50 $mA/cm^2$, a high luminosity of 2842 $cd/m^2$, a luminescent efficiency of 4.65 cd/A, and a half-life span of 167 hours at 100 $mA/cm^2$.

Example 3

An organic light-emitting device was manufactured in the same manner as in Example 1, except that Compound 32 was used instead of Compound 22 to form the EML.

The organic light-emitting device had a driving voltage of 6.28 V at a current density of 50 $mA/cm^2$, a high luminosity of 2157 $cd/m^2$, a luminescent efficiency of 4.85 cd/A, and a half-life span of 197 hours at 100 $mA/cm^2$.

Example 4

An organic light-emitting device was manufactured in the same manner as in Example 1, except that Compound 39 was used instead of Compound 22 to form the EML.

The organic light-emitting device had a driving voltage of 6.33 V at a current density of 50 $mA/cm^2$, a high luminosity of 2563 $cd/m^2$, a luminescent efficiency of 5.34 cd/A, and a half-life span of 184 hours at 100 $mA/cm^2$.

Example 5

An organic light-emitting device was manufactured in the same manner as in Example 1, except that DPVBi was used as a blue fluorescent dopant and the Compound 18 was used instead of $Alq_3$ to form the ETL on the EML.

The organic light-emitting device had a driving voltage of 5.98 V at a current density of 50 $mA/cm^2$, a high luminosity of 2716 $cd/m^2$, a luminescent efficiency of 5.08 cd/A, and a half-life span of 190 hours at 100 $mA/cm^2$.

Example 6

An organic light-emitting device was manufactured in the same manner as in Example 1, except that the Compound 19 was used instead of Compound 18 to form the ETL.

The organic light-emitting device had a driving voltage of 6.27 V at a current density of 50 $mA/cm^2$, a high luminosity of 2421 cd/m², a luminescent efficiency of 5.95 cd/A, and a half-life span of 209 hours at 100 mA/cm².

Example 7

An organic light-emitting device was manufactured in the same manner as in Example 1, except that Compound 22 was used as a blue fluorescent dopant to form the EML, and then Compound 18 was used instead of $Alq_3$ to form the ETL.

The organic light-emitting device had a driving voltage of 5.91 V at a current density of 50 mA/cm², a high luminosity of 3014 cd/m², a luminescent efficiency of 6.04 cd/A, and a half-life span of 221 hours at 100 mA/cm².

Example 8

An organic light-emitting device was manufactured in the same manner as in Example 1, except that Compound 19 was used instead of $Alq_3$ to form the ETL.

The organic light-emitting device had a driving voltage of 5.73 V at a current density of 50 mA/cm², a high luminosity of 3102 cd/m², a luminescent efficiency of 6.29 cd/A, and a half-life span of 232 hours at 100 mA/cm².

Comparative Example 1

An organic light-emitting device was manufactured in the same manner as in Example 1, except that a blue fluorescent dopant DPVBi was used instead of Compound 2 to form the EML.

The organic light-emitting device had a driving voltage of 7.35 V at a current density of 50 mA/cm², a high luminosity of 1490 cd/m², a luminescent efficiency of 3.14 cd/A, and a half-life span of 120 hours at 100 mA/cm².

The organic light-emitting devices including the above-described heterocyclic compounds as a dopant or an electron-transporting material had a driving voltage that was lower by 1.6 V or greater than devices manufactured using DPVBi and $Alq_3$, and thus had higher efficiency and good I-V-L characteristics. In particular, luminosity and lifetime characteristics were markedly improved.

The organic light-emitting devices of Examples 1 through 4 manufactured by using the above-described heterocyclic compounds as a dopant had a driving voltage that was lowered by 0.7 V or greater than the organic light-emitting device of Comparative Example 1. In addition, luminosity and lifetime characteristics were markedly improved compared to the organic light-emitting device of Comparative Example 1.

The organic light-emitting devices of Examples 5 and 6 manufactured by using the above-described heterocyclic compounds as an electron-transporting material had a driving voltage that was lowered by 1 V or greater than the organic light-emitting device of Comparative Example 1. In addition, luminosity and lifetime characteristics were markedly improved compared to the organic light-emitting device of Comparative Example 1.

The organic light-emitting devices of Examples 7 and 8 manufactured by using the above-described heterocyclic compounds as a dopant and an electron-transporting material had a driving voltage that was lowered by 1.4 V or greater than the organic light-emitting device of Comparative Example 1. In addition, luminescent efficiency was improved by about 200% than the organic light-emitting device of Comparative Example 1. The device characteristics and lifetime characteristics of the organic light-emitting devices of Examples 1 through 8 and Comparative Example 1 are tabled in Table 1 below.

TABLE 1

|  | EML or electron-transporting material | Driving Voltage (V) | Current density (mA/cm²) | Luminocity (cd/cm²) | Luminescent efficiency (cd/A) | Color of light | half-life span (hr @100 mA/cm²) |
| --- | --- | --- | --- | --- | --- | --- | --- |
| Example 1 | Compound 22 | 6.59 | 50 | 2,395 | 4.97 | blue | 172 hr |
| Example 2 | Compound 37 | 6.51 | 50 | 2,378 | 4.75 | blue | 167 hr |
| Example 3 | Compound 32 | 6.28 | 50 | 2,157 | 4.31 | blue | 197 hr |
| Example 4 | Compound 39 | 6.38 | 50 | 2,560 | 5.12 | blue | 184 hr |
| Example 5 | Compound 18 | 5.98 | 50 | 2,716 | 5.43 | blue | 190 hr |
| Example 6 | Compound 19 | 6.27 | 50 | 2,421 | 4.84 | blue | 209 hr |
| Example 7 | Dopant Compound 22, ETL Compound 18 | 5.91 | 50 | 3,014 | 6.03 | blue | 221 hr |
| Example 8 | Dopant Compound 39, ETL Compound 19 | 5.63 | 50 | 3,105 | 6.21 | blue | 232 hr |
| Comparative Example 1 | DPVBi | 7.35 | 50 | 1,490 | 3.14 | blue | 120 hr |

The heterocyclic compounds according to embodiments of the present invention have good light emitting characteristics and charge transporting capability, and thus, may be used as electron injecting or transporting materials that are suitable for any color fluorescent or phosphorescent devices, such as red, green, blue, and white fluorescent or phosphorescent devices, and may be used as light emitting materials for green, blue, or white fluorescent devices. Therefore, organic light-emitting devices having high efficiency, low driving voltages, high luminance, and long lifetime may be manufactured using the heterocyclic compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 2 below:

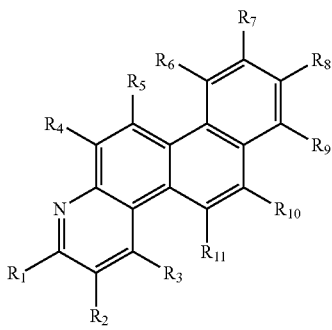

[Formula 2]

$R_1$, $R_2$, $R_3$, $R_5$, $R_6$, $R_7$, $R_8$, $R_9$ and $R_{11}$ each being independently a hydrogen atom or a deuterium atom, and $R_4$ and $R_{10}$ are each independently a hydrogen atom, a deuterium atom, a halogen atom, a cyano group, a substituted or unsubstituted $C_1$-$C_{20}$ alkyl group, or groups represented by Formulae 2a to 2g below:

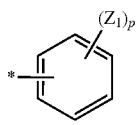   2a

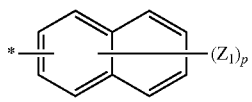   2b

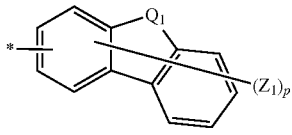   2c

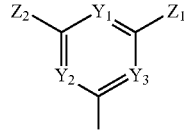   2d

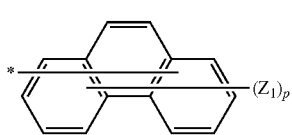   2e

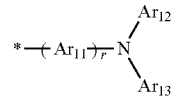   2f

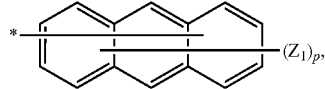   2g $Q_1$ is a linking group selected from among —C($R_{19}$)($R_{20}$)—, —N($R_{21}$)—, —S— and —O—; $Y_1$, $Y_2$ and $Y_3$ are each independently a linking group selected from among —N= and —C($R_{22}$)=; $Z_1$, $Z_2$, $Ar_{12}$, $Ar_{13}$, $R_{19}$, $R_{20}$, $R_{21}$ and $R_{22}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; $Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group; $R_1$ to $R_{11}$ are not all hydrogen atoms; p is an integer from 1 to 7; r is an integer from 0 to 5; and * indicates a binding site.

2. The heterocyclic compound of claim 1, $R_1$, $R_2$, $R_3$, $R_5$, $R_6$, $R_7$, $R_8$, $R_9$ and $R_{11}$ are each independently a hydrogen atom and a deuterium atom, and $R_4$ and $R_{10}$ are each independently a hydrogen atom, a deuterium atom, a halogen atom, a cyano group, a methyl group, an ethyl group, a propyl group, a butyl group, a pentyl group, or groups represented by Formulae 3a to 3c below:

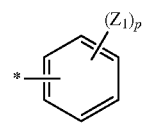   3a

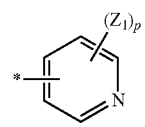   3b

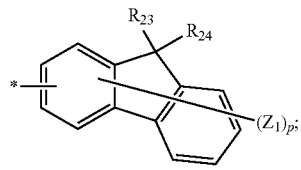   3c $Z_1$, $R_{23}$ and $R_{24}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ fused polycyclic group, a halogen atom, a cyano group, a nitro group, a hydroxyl group, or a carboxyl group; $R_1$ to $R_{11}$ are not all hydrogen atoms; p is an integer from 1 to 7; and * indicates a binding site.

3. The heterocyclic compound of claim 1, the heterocyclic compound being any one of compounds below:

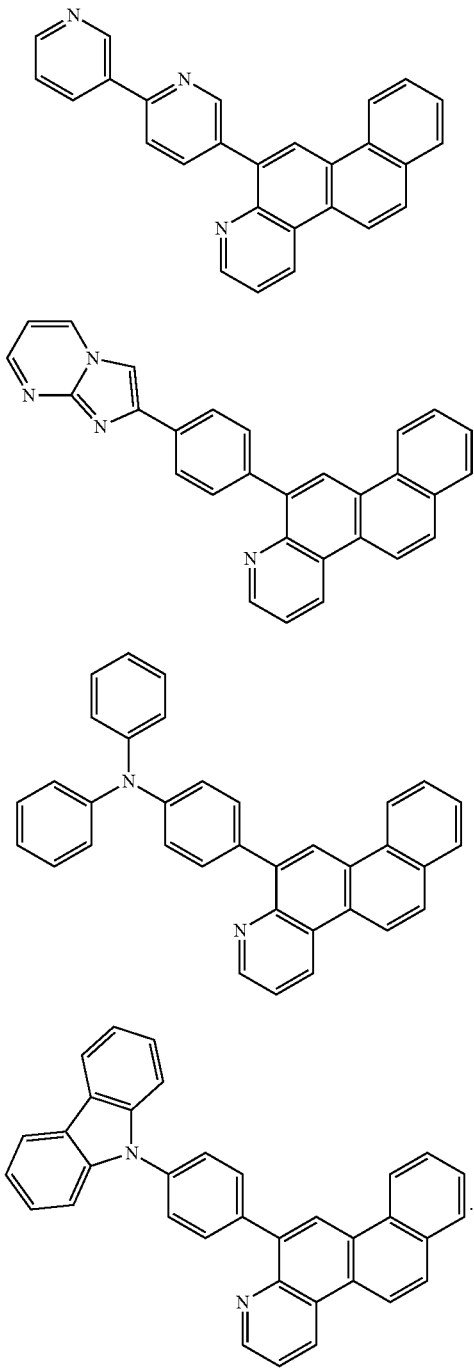

4. An organic light-emitting device comprising:
a first electrode;
a second electrode; and
an organic layer interposed between the first electrode and the second electrode,
the organic layer comprising a first layer comprised of the heterocyclic compound of claim 1.

5. The organic light-emitting device of claim 4, wherein the first layer comprises: a hole injection layer (HIL), a hole transport layer (HTL), a layer having both a hole injection function and a hole transport function, an electron injection layer (EIL), an electron transport layer (ETL) or a layer having both an electron injection function and an electron transport function.

6. The organic light-emitting device of claim 4, the first layer comprising a hole injection layer (HIL), a hole transport layer (HTL), a layer having both a hole injection function and a hole transport function, an emission layer (EML), an electron injection layer (EIL), an electron transport layer (ETL), or a layer having both an electron injection function and an electron transport function, the first layer further comprising a charge-generating material.

7. The organic light-emitting device of claim 4, wherein the first layer is an emission layer (EML), and the heterocyclic compound is used as a host or a dopant.

8. The organic light-emitting device of claim 4, wherein the first layer is an emission layer (EML), and the emission layer further comprises an anthracene compound, an arylamine compound or a styryl compound.

9. The organic light-emitting device of claim 4, wherein the first layer is an emission layer (EML) comprising at least one layer of a red layer, a green layer, a blue layer, and a white layer, and at least one of said at least one layer comprises a phosphorescence compound.

10. The organic light-emitting device of claim 4, wherein the first layer is a blue emission layer.

11. The organic light-emitting device of claim 4, wherein the first layer is a blue emission layer, and the heterocyclic compound is used as a blue dopant.

12. The organic light-emitting device of claim 4, wherein the organic layer further comprises a hole injection layer (HIL), a hole transport layer (HTL), a layer having both a hole injection function and a hole transport function, an emission layer (EML), a hole block layer (HBL), an electron transport layer (ETL), an electron injection layer (EIL), or a combination of at least two thereof.

13. The organic light-emitting device of claim 4, the first layer being formed by using a wet method using the heterocyclic compound of claim 1.

14. A flat panel display device comprising the organic light-emitting device of claim 4, wherein the first electrode of the organic light-emitting device is electrically connected to a source electrode or a drain electrode of a thin film transistor.

* * * * *